United States Patent
Stahmann

(10) Patent No.: US 9,623,251 B2
(45) Date of Patent: Apr. 18, 2017

(54) MULTI-CHAMBER LEADLESS PACEMAKER SYSTEM WITH INTER-DEVICE COMMUNICATION

(71) Applicant: Cardiac Pacemakers, Inc., St. Paul, MN (US)

(72) Inventor: Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/618,536

(22) Filed: Feb. 10, 2015

(65) Prior Publication Data
US 2015/0224315 A1     Aug. 13, 2015

Related U.S. Application Data

(60) Provisional application No. 61/938,024, filed on Feb. 10, 2014.

(51) Int. Cl.
*A61N 1/00*     (2006.01)
*A61N 1/368*     (2006.01)
(Continued)

(52) U.S. Cl.
CPC ......... *A61N 1/3684* (2013.01); *A61N 1/3682* (2013.01); *A61N 1/36592* (2013.01);
(Continued)

(58) Field of Classification Search
CPC .. A61N 1/3622; A61N 1/3624; A61N 1/3684; A61N 1/3682; A61N 1/368; A61N 1/3688
See application file for complete search history.

(56) References Cited

U.S. PATENT DOCUMENTS 4,624,260 A * 11/1986 Baker, Jr. ............. A61N 1/3622
607/12
7,062,328 B1 * 6/2006 Levine ................... A61N 1/362
607/27
(Continued)

FOREIGN PATENT DOCUMENTS

WO     2013080038 A2     6/2013

OTHER PUBLICATIONS

Boston Scientific. "A Closer Look: Pacemaker-Mediated Tachycardia (PMT) and Daul-Chamber Pacemakers and Defibrillators." (6 pages). Jun. 25, 2012.

*Primary Examiner* — Scott Getzow
(74) *Attorney, Agent, or Firm* — Seager, Tufte & Wickhem, LLP.

(57) ABSTRACT

Systems and methods for switching modes in a multi-device medical system. In one example, a first leadless cardiac pacemaker (LCP) may be implantable at a ventricular site, and a second leadless cardiac pacemaker (LCP) may be implantable at an atrial site and configured to sensing atrial contractions. The first LCP and the second LCP may be configured to be communicatively coupled such that the first LCP and the second LCP can deliver pacing therapy to the ventricular site in a tracking mode. The first LCP and/or the second LCP may additionally be configured to deliver pacing therapy to the ventricular site in a non-tracking mode if an interval between atrial contractions sensed by the second LCP becomes shorter than a threshold duration.

19 Claims, 13 Drawing Sheets

(51) Int. Cl.
- *A61N 1/365* (2006.01)
- *A61N 1/372* (2006.01)
- *A61N 1/375* (2006.01)
- *A61N 1/362* (2006.01)

(52) U.S. Cl.
CPC ....... *A61N 1/3756* (2013.01); *A61N 1/37205* (2013.01); *A61N 1/37288* (2013.01); *A61N 1/3622* (2013.01); *A61N 1/3624* (2013.01)

(56) References Cited

U.S. PATENT DOCUMENTS

| | | |
|---|---|---|
| 7,558,631 B2 | 7/2009 | Cowan et al. |
| 7,610,092 B2 | 10/2009 | Cowan et al. |
| 7,996,087 B2 | 8/2011 | Cowan et al. |
| 8,315,701 B2 | 11/2012 | Cowan et al. |
| 8,571,678 B2 | 10/2013 | Wang |
| 8,744,572 B1 | 6/2014 | Greenhut et al. |
| 2006/0136004 A1 | 6/2006 | Cowan et al. |
| 2007/0078490 A1 | 4/2007 | Cowan et al. |
| 2007/0088397 A1* | 4/2007 | Jacobson ............. A61N 1/3704 607/9 |
| 2010/0063562 A1 | 3/2010 | Cowan et al. |
| 2010/0228308 A1 | 9/2010 | Cowan et al. |
| 2012/0316613 A1 | 12/2012 | Keefe et al. |
| 2013/0079861 A1 | 3/2013 | Reinert et al. |
| 2013/0123872 A1 | 5/2013 | Bornzin et al. |
| 2013/0282073 A1 | 10/2013 | Cowan et al. |
| 2013/0325081 A1 | 12/2013 | Karst et al. |
| 2014/0214104 A1 | 7/2014 | Greenhut et al. |

* cited by examiner

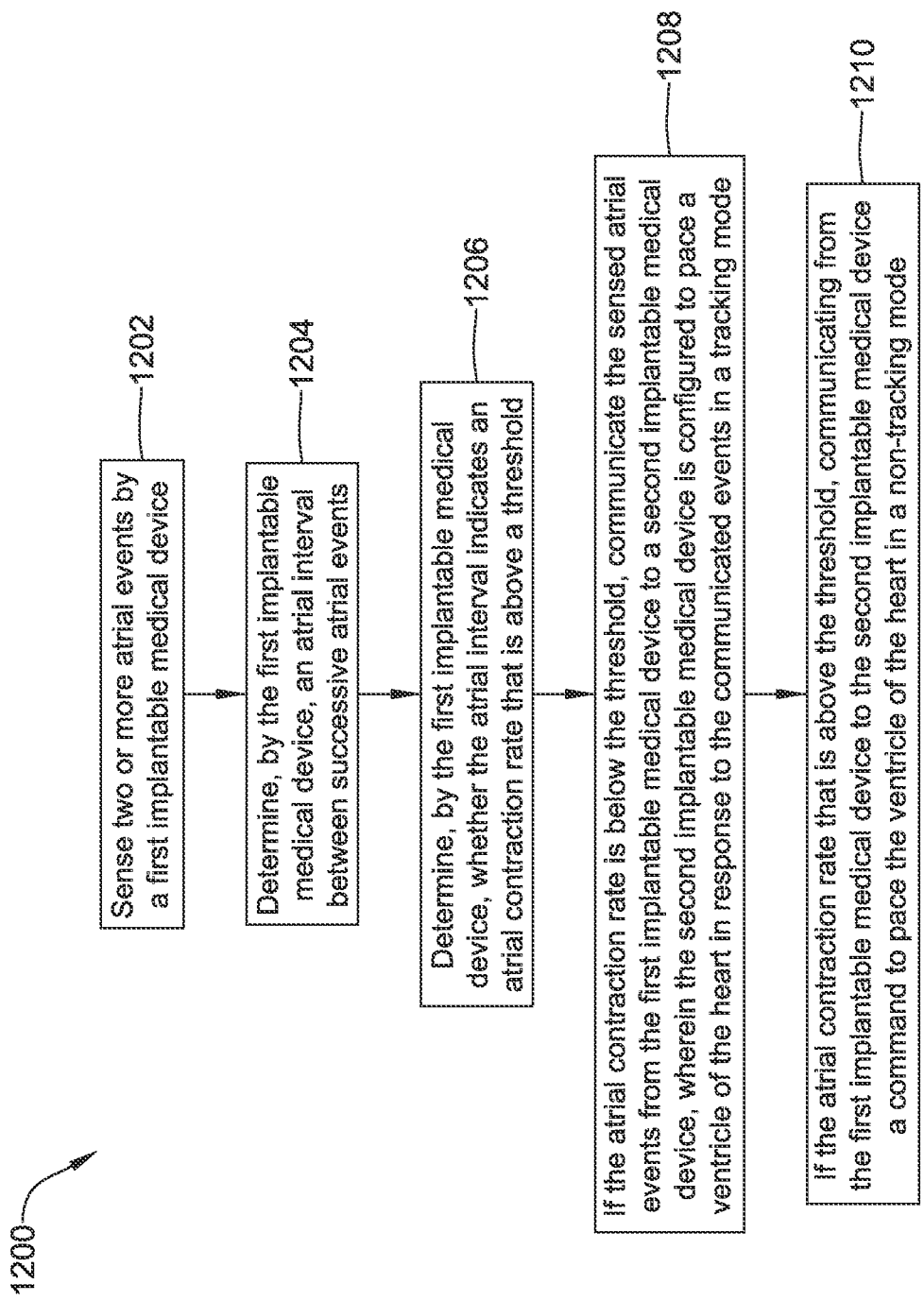

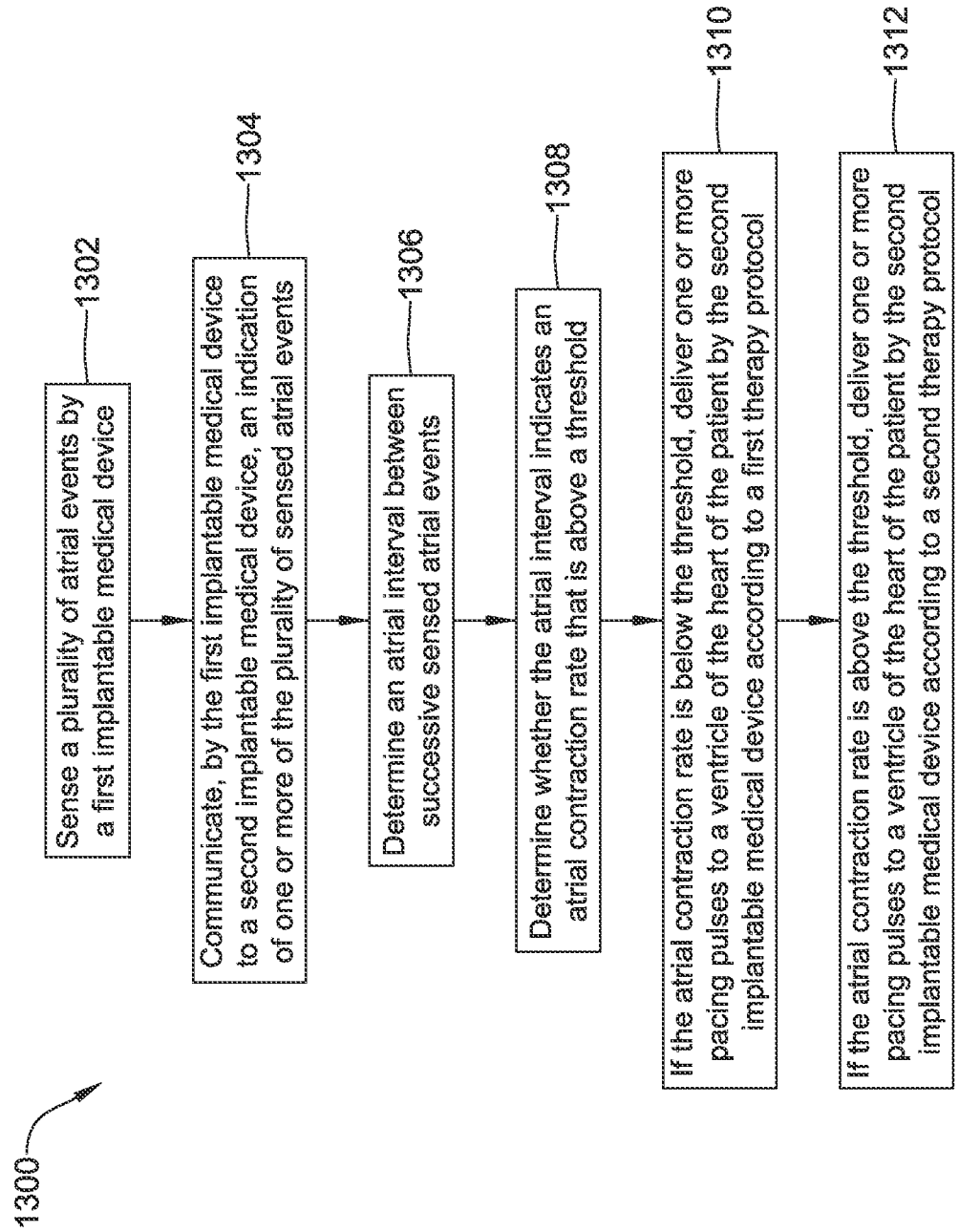

MULTI-CHAMBER LEADLESS PACEMAKER SYSTEM WITH INTER-DEVICE COMMUNICATION

CROSS-REFERENCE TO RELATED APPLICATIONS

This application claims priority under 35 U.S.C. §119 to U.S. Provisional Application Ser. No. 61/938,024, filed Feb. 10, 2014, the entirety of which is incorporated herein by reference.

TECHNICAL FIELD

The present disclosure generally relates to pacemakers, and more particularly, to systems and methods for coordinating detection and/or treatment of abnormal heart activity using multiple implanted devices within a patient.

BACKGROUND

Pacemakers can be used to treat patients suffering from various heart conditions that can result in reduced ability of the heart to deliver sufficient amounts of blood to a patient's body. In some cases, heart conditions can lead to rapid, irregular, and/or inefficient heart contractions. To help alleviate some of these conditions, various devices (e.g., pacemakers, defibrillators, etc.) can be implanted in a patient's body. Such devices are often used to monitor heart activity and provide electrical stimulation to the heart to help the heart operate in a more normal, efficient and/or safe manner.

SUMMARY

The present disclosure relates generally to systems and methods for coordinating detection and/or treatment of abnormal heart activity using multiple implanted devices within a patient. In some cases, the devices may be implanted within separate chambers of the heart and may communicate information between the various devices for improving detection and treatment of cardiac rhythm abnormalities. It is contemplated that the multiple implanted devices may include, for example, pacemakers with leads, leadless pacemakers, defibrillators, sensors, neuro-stimulators, and/or any other suitable implantable devices, as desired.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which:

FIG. 12 is a flow diagram of an illustrative method that may be implemented by a medical device system, such as those medical device systems described with respect to FIGS. 3-6; and FIG. 13 is a flow diagram of another illustrative method that may be implemented by a medical device system, such as those medical device systems described with respect to FIGS. 3-6.

Figure 1:
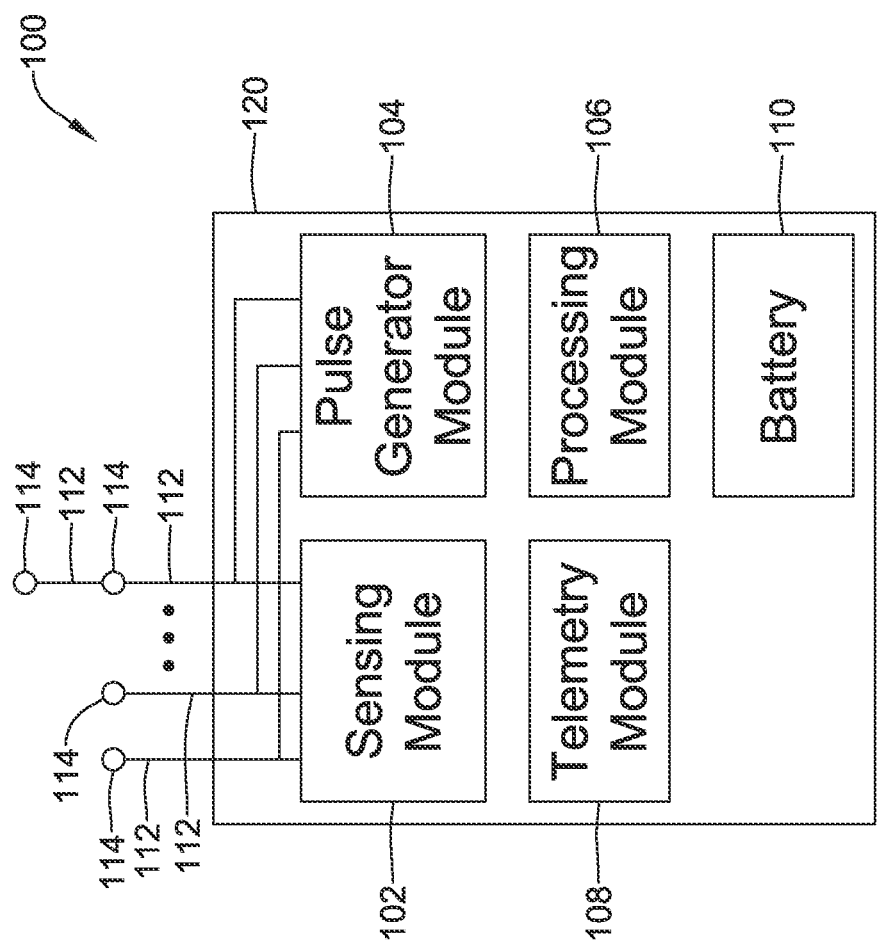
FIG. 1 illustrates a block diagram of an exemplary medical device that may be used in accordance with various examples of the present disclosure.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

Normal, healthy hearts operate by coordinating contraction of the atria and the ventricles. For example, the atria of a heart normally contract first, thereby forcing blood into corresponding ventricles. Only after the blood has been pumped into the ventricles do the ventricles contract, forcing the blood into the arteries and throughout the body. Various conditions may cause such coordinated contraction to become un-synchronized in a patient. Synchronized contractions across the chambers of the heart can help increase the pumping capacity of the heart. In some cases, the atrial may start to beat too fast, and sometimes fibrillate. During these periods, it may be desirable to not synchronize the ventricle with the atrium and pace the ventricle independent of the atrium.

In order to assist patients who experience constant or intermittent un-synchronized contractions, various medical devices may be used to sense when uncoordinated contractions occur and to deliver electrical pacing therapy to the various chambers of the heart in order to coordinate the contractions. For example, medical device systems may be used to sense generated or conducted cardiac electrical signals that are indicative of a chamber contraction. In some cases, such medical device systems may be used to detect such signals in different chambers of the heart in order to distinguish between, for example, atrial and ventricular contractions. In some cases, such systems may deliver electrical stimulation, for example pacing pulses, to help the chambers contract in a more synchronous manner.

In some cases, a ventricle may be paced a predetermined time after detecting an atrial contraction in a tracking mode. However, when abnormal atrial contractions are detected, such as atrial contraction rates that are too slow or too fast, the system may be switched to pace the ventricle in a non-tracking mode. If the ventricle were continued to be paced in the tracking mode, the contraction rate of the ventricles may become dangerously high or dangerously low.

Multi-device systems can introduce unique challenges for implementing multi-chamber therapy. In multi-device systems, two separate devices may be responsible for sensing cardiac events in different chambers and delivering electrical stimulation to the different chambers. In some instances, each of the devices may be able to detect and/or deliver electrical stimulation to one chamber of the heart. The multiple devices of such systems may be configured to communicate sensed cardiac events and other information to the other devices in order to safely and effectively deliver electrical stimulation to the various chambers.

FIG. 1 illustrates a block diagram of an exemplary medical device 100 (referred to hereinafter as, MD 100) that may be used in accordance with various examples of the present disclosure. In some cases, the MD 100 may be used for sensing cardiac events, determining occurrences of arrhythmias, and delivering electrical stimulation. In some instances, MD 100 can be implanted within a patient's body, at a particular location (e.g., in close proximity to the patient's heart), to sense and/or regulate the cardiac events of the heart. In other examples, MD 100 may be located externally to a patient to sense and/or regulate the cardiac events of the heart. Cardiac contractions generally result from electrical signals that are intrinsically generated by a heart. These electrical signals conduct through the heart tissue, causing the muscle cells of the heart to contract. MD 100 may include features that allow MD 100 to sense such generated or conducted cardiac electrical signals, or cardiac contractions that result from such signals, any of which may generally be termed "cardiac events." In at least some examples, MD 100 may additionally include features that allow MD 100 to sense other physical parameters (e.g. mechanical contraction, heart sounds, blood pressure, blood-oxygen levels, etc.) of the heart. MD 100 may include the ability to determine a heart rate and/or occurrences of arrhythmias based on the sensed cardiac events or other physiological parameters.

In some examples, MD 100 may be able to deliver electrical stimulation to the heart in order to ensure synchronized contractions or to treat any detected arrhythmias. Some example arrhythmias include un-synchronized contractions between the atria and ventricles of the heart, bradyarrhythmias, tachyarrhythmias, and fibrillation. For example, MD 100 may be configured to deliver electrical stimulation, such as pacing pulses, defibrillation pulses, or the like, in order to implement one or more therapies. Some example of such therapies may include multi-chamber therapy, e.g. ensuring synchronized contraction of the various chambers of the heart, bradycardia therapy, ATP therapy, CRT, defibrillation, or other electrical stimulation therapies in order to treat one or more arrhythmias. In some examples, MD 100 coordinates with one or more separate devices in order to deliver one or more therapies.

FIG. 1 is an illustration of one example medical device 100. The illustrative MD 100 may include a sensing module 102, a pulse generator module 104, a processing module 106, a telemetry module 108, and a battery 110, all housed within a housing 120. MD 100 may further include leads 112, and electrodes 114 attached to housing 120 and in electrical communication with one or more of the modules 102, 104, 106, and 108 housed within housing 120.

Leads 112 may be connected to and extend away from housing 120 of MD 100. In some examples, leads 112 are implanted on or within the heart of the patient. Leads 112 may contain one or more electrodes 114 positioned at various locations on leads 112 and distances from housing 120. Some leads 112 may only include a single electrode 114 while other leads 112 may include multiple electrodes 114. Generally, electrodes 114 are positioned on leads 112 such that when leads 112 are implanted within the patient, one or more electrodes 114 are in contact with the patient's cardiac tissue. Accordingly, electrodes 114 may conduct received cardiac electrical signals to leads 112. Leads 112 may, in turn, conduct the received cardiac electrical signals to one or more modules 102, 104, 106, and 108 of MD 100. In a similar manner, MD 100 may generate electrical stimulation, and leads 112 may conduct the generated electrical stimulation to electrodes 114. Electrodes 114 may then conduct the generated electrical stimulation to the cardiac tissue of the patient. When discussing sensing cardiac electrical signals and delivering generated electrical stimulation, this disclosure may consider such conduction implicit in those processes.

Sensing module 102 may be configured to sense the cardiac electrical events. For example, sensing module 102 may be connected to leads 112 and electrodes 114 through leads 112 and sensing module 102 may be configured to receive cardiac electrical signals, e.g. cardiac events, conducted through electrodes 114 and leads 112. In some examples, leads 112 may include various sensors, such as accelerometers, blood pressure sensors, heart sound sensors, blood-oxygen sensors, and other sensors which measure physiological parameters of the heart and/or patient. In other examples, such sensors may be connected directly to sensing module 102 rather than to leads 112. In any case, sensing module 102 may be configured to receive such signals produced by any sensors connected to sensing module 102, either directly or through leads 112. Sensing module 102 may additionally be connected to processing module 106 and may be configured to communicate such received signals to processing module 106. In some examples sensing module 102 is configured to sense cardiac electrical events from only the chamber in which MD 100 is affixed. In other examples sensing module 102 is configured to sense cardiac electrical events from the chamber in which MD 100 is affixed and from other chambers of heart 110.

Pulse generator module 104 may be connected to electrodes 114. In some examples, pulse generator module 104 may be configured to generate electrical stimulation signals to provide electrical stimulation to the heart. For example, pulse generator module 104 may generate such electrical stimulation signals by using energy stored in battery 110 within MD 100. Pulse generator module 104 may be configured to generate electrical stimulation signals in order to provide one or multiple of a number of different therapies. For example, pulse generator module 104 may be configured to generate electrical stimulation signals to provide multi-chamber therapies, bradycardia therapy, tachycardia therapy, cardiac resynchronization therapy, and fibrillation therapy. Multi-chamber therapies may include techniques for detecting un-synchronized contractions of the heart and coordinating a delivering of electrical stimulation signals to the various chambers of the heart in order to help ensure synchronization of contractions. Bradycardia therapy may include generating and delivering pacing pulses at a rate faster than the intrinsically generated electrical signals in order to try to increase the heart rate. Tachycardia therapy may include ATP therapy. Cardiac resynchronization therapy may include delivering electrical stimulation to both ventricles of the heart in order to produce a more efficient contraction of the ventricles. Fibrillation therapy may include delivering a fibrillation pulse to try to override the heart and stop the fibrillation state. In other examples, pulse generator 104 may be configured to generate electrical stimulation signals to provide different electrical stimulation therapies to treat one or more detected arrhythmias and/or other heart conditions.

Processing module 106 can be configured to control the operation of MD 100. For example, processing module 106 may be configured to receive electrical signals from sensing module 102. Based on the received signals, processing module 106 may be able to determine a heart rate. In at least some examples, processing module 106 may be configured to determine occurrences of arrhythmias, based on the heart rate, various features of the received signals, or both. Based on any determined arrhythmias, processing module 106 may be configured to control pulse generator module 104 to generate electrical stimulation in accordance with one or more therapies to treat the determined one or more arrhythmias. Processing module 106 may further receive information from telemetry module 108. In some examples, processing module 106 may use such received information in determining whether an arrhythmia is occurring or to take particular action in response to the information. Processing module 106 may additionally control telemetry module 108 to send information to other devices.

In some examples, processing module 106 may include a pre-programmed chip, such as a very-large-scale integration (VLSI) chip or an application specific integrated circuit (ASIC). In such embodiments, the chip may be pre-programmed with control logic in order to control the operation of MD 100. By using a pre-programmed chip, processing module 106 may use less power than other programmable circuits while able to maintain basic functionality, thereby increasing the battery life of MD 100. In other examples, processing module 106 may include a programmable microprocessor. Such a programmable microprocessor may allow a user to adjust the control logic of MD 100, thereby allowing for greater flexibility of MD 100 than when using a pre-programmed chip. In some examples, processing module 106 may further include a memory circuit and processing module 106 may store information on and read information from the memory circuit. In other examples, MD 100 may include a separate memory circuit (not shown) that is in communication with processing module 106, such that processing module 106 may read and write information to and from the separate memory circuit.

Telemetry module 108 may be configured to communicate with devices such as sensors, other medical devices, or the like, that are located externally to MD 100. Such devices may be located either external or internal to the patient's body. Irrespective of the location, external devices (i.e. external to the MD 100 but not necessarily external to the patient's body) can communicate with MD 100 via telemetry module 108 to accomplish one or more desired functions. For example, MD 100 may communicate sensed electrical signals to an external medical device through telemetry module 108. The external medical device may use the communicated electrical signals in determining a heart rate and/or occurrences of arrhythmias or in coordinating its function with MD 100. MD 100 may additionally receive sensed electrical signals from the external medical device through telemetry module 108, and MD 100 may use the received sensed electrical signals in determining a heart rate and/or occurrences of arrhythmias or in coordinating its function with MD 100. Telemetry module 108 may be configured to use one or more methods for communicating with external devices. For example, telemetry module 108 may communicate via radiofrequency (RF) signals, inductive coupling, optical signals, acoustic signals, conducted communication signals, or any other signals suitable for communication. Communication techniques between MD 100 and external devices will be discussed in further detail with reference to FIG. 3 below.

Battery 110 may provide a power source to MD 100 for its operations. In one example, battery 110 may be a non-rechargeable lithium-based battery. In other examples, the non-rechargeable battery may be made from other suitable materials known in the art. Because, in examples where MD 100 is an implantable device, access to MD 100 may be limited, it is necessary to have sufficient capacity of the battery to deliver sufficient therapy over a period of treatment such as days, weeks, months, or years. In other examples, battery 110 may a rechargeable lithium-based battery in order to facilitate increasing the useable lifespan of MD 100.

In some examples, MD 100 may be an implantable cardiac pacemaker (ICP). In such an example, MD 100 may have one or more leads, for example leads 112, which are implanted on or within the patient's heart. The one or more leads 112 may include one or more electrodes 114 that are in contact with cardiac tissue and/or blood of the patient's heart. MD 100 may also be configured to sense cardiac events and determine, for example, a heart rate and/or one or more cardiac arrhythmias based on analysis of the sensed cardiac events. MD 100 may further be configured to deliver multi-chamber therapy, CRT, ATP therapy, bradycardia therapy, defibrillation therapy and/or other therapy types via leads 112 implanted within the heart. In at least some examples, MD 100 may be configured to deliver therapy separately to multiple chambers of the heart, either alone or in combination with one or more other devices.

Figure 2:
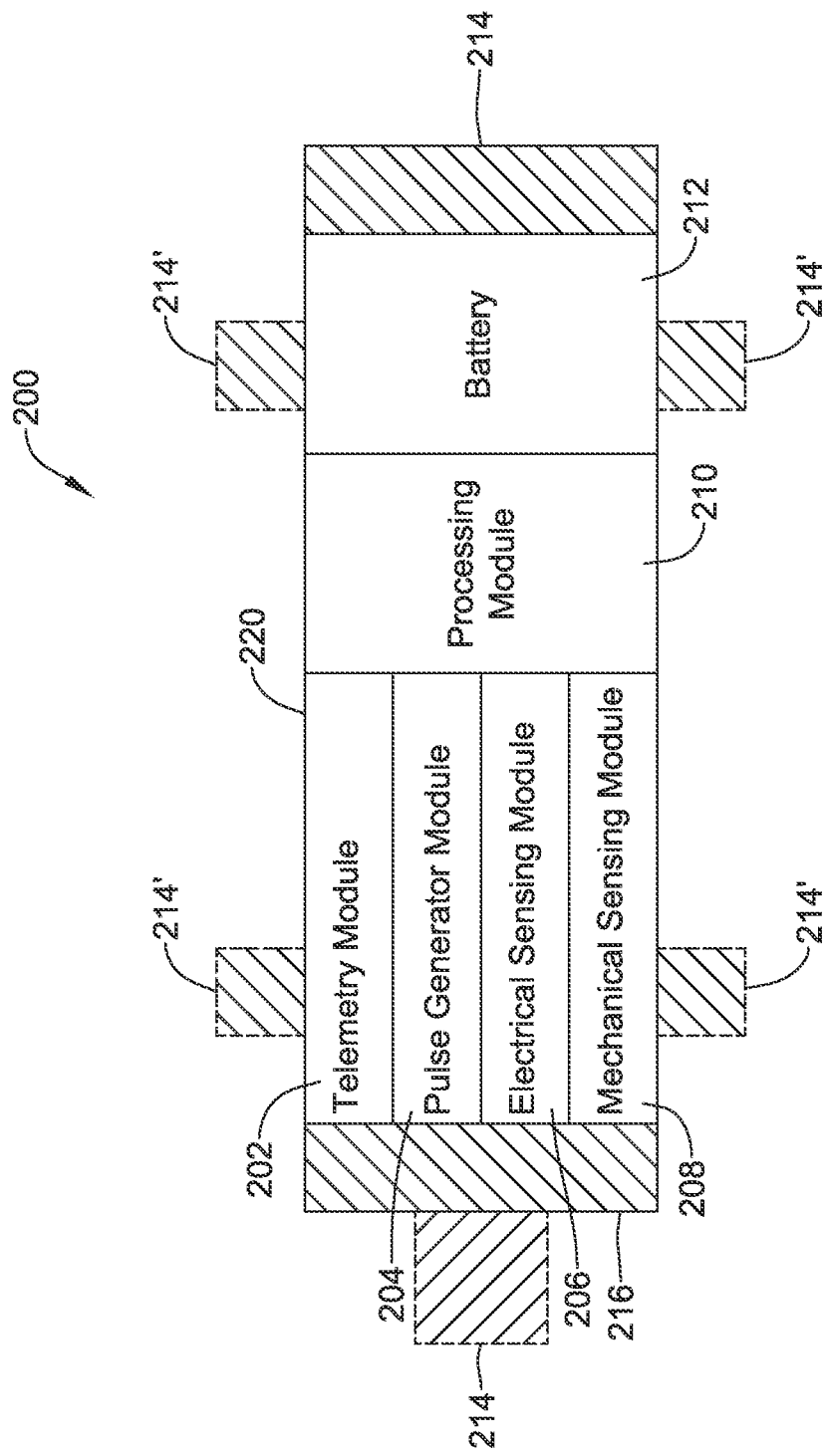
FIG. 2 illustrates an exemplary leadless cardiac pacemaker (LCP) having electrodes, according to one example of the present disclosure.

In other examples, MD 100 may be a leadless cardiac pacemaker (LCP—described more specifically with respect to FIG. 2). In such examples, MD 100 may not include leads 112 that extend away from housing 120. Rather, MD 100 may include electrodes 114 coupled relative to the housing 120. In these examples, MD 100 may be implanted on or within the patient's heart at a desired location.

FIG. 2 is an illustration of an exemplary leadless cardiac pacemaker (LCP) 200. In the example shown, LCP 200 may include all of the modules and components of MD 100, except that LCP 200 may not include leads 112. As can be seen in FIG. 2, LCP 200 may be a compact device with all components housed within LCP 200 or directly on housing 220. As illustrated in FIG. 2, LCP 200 may include telemetry module 202, pulse generator module 204, processing module 210, and battery 212. Such components may have a similar function to the similarly named modules and components as discussed in conjunction with MD 100 of FIG. 1.

In some examples, LCP 200 may include electrical sensing module 206 and mechanical sensing module 208. Electrical sensing module 206 may be similar to sensing module 102 of MD 100. For example, electrical sensing module 206 may be configured to sense or receive cardiac events. Electrical sensing module 206 may be in electrical connection with electrodes 214 and/or 214', which may conduct the cardiac events to electrical sensing module 206. Mechanical sensing module 208 may be configured to receive one or more signals representative of one or more physiological parameters of the heart. For example, mechanical sensing module 208 may include, or be in electrical communication with one or more sensors, such as accelerometers, blood pressure sensors, heart sound sensors, blood-oxygen sensors, and other sensors which measure physiological parameters of the patient. Although described with respect to FIG. 2 as separate sensing modules, in some examples, electrical sensing module 206 and mechanical sensing module 208 may be combined into a single module.

In at least one example, each of modules 202, 204, 206, 208, and 210 illustrated in FIG. 2 may be implemented on a single integrated circuit chip. In other examples, the illustrated components may be implemented in multiple integrated circuit chips that are in electrical communication with one another. All of modules 202, 204, 206, 208, and 210 and battery 212 may be encompassed within housing 220. Housing 220 may generally include any material that is known as safe for implantation within a human body and may hermetically seal modules 202, 204, 206, 208, and 210 and battery 212 from fluids and tissues when LCP 200 is implanted within a patient.

As depicted in FIG. 2, LCP 200 may include electrodes 214, which can be secured relative to housing 220 but exposed to the tissue and/or blood surrounding the LCP 200. As such, electrodes 214 may be generally disposed on either end of LCP 200 and may be in electrical communication with one or more of modules 202, 204, 206, 208, and 210. In some examples, electrodes 214 may be connected to housing 220 only through short connecting wires such that electrodes 214 are not directly secured relative to housing 220. In some examples, LCP 200 may additionally include one or more electrodes 214'. Electrodes 214' may be positioned on the sides of LCP 200 and increase the number of electrodes by which LCP 200 may sense cardiac electrical activity and/or deliver electrical stimulation. Electrodes 214 and/or 214' can be made up of one or more biocompatible conductive materials such as various metals or alloys that are known to be safe for implantation within a human body. In some instances, electrodes 214 and/or 214' connected to LCP 200 may have an insulative portion that electrically isolates the electrodes 214 from, adjacent electrodes, the housing 220, and/or other materials.

To implant LCP 200 inside patient's body, an operator (e.g., a physician, clinician, etc.), may need to fix LCP 200 to the cardiac tissue of the patient's heart. To facilitate fixation, LCP 200 may include one or more anchors 216. Anchor 216 may be any one of a number of fixation or anchoring mechanisms. For example, anchor 216 may include one or more pins, staples, threads, screws, helix, tines, and/or the like. In some examples, although not shown, anchor 216 may include threads on its external surface that may run along at least a partial length of anchor 216. The threads may provide friction between the cardiac tissue and the anchor to help fix anchor 216 within the cardiac tissue. In other examples, anchor 216 may include other structures such as barbs, spikes, or the like to facilitate engagement with the surrounding cardiac tissue.

The design and dimensions of MD 100 and LCP 200, as shown in FIGS. 1 and 2, respectively, can be selected based on various factors. For example, if the medical device is for implant on the endocardial tissue, such as is sometimes the case of an LCP, the medical device can be introduced through a femoral vein into the heart. In such instances, the dimensions of the medical device may be such as to be navigated smoothly through the tortuous path of the vein without causing any damage to surrounding tissue of the vein. According to one example, the average diameter of the femoral vein may be between about 4 mm to about 8 mm in width. For navigation to the heart through the femoral vein, the medical device can have a diameter of at less than 8 mm. In some examples, the medical device can have a cylindrical shape having a circular cross-section. However, it should be noted that the medical device can be made of any other suitable shape such as rectangular, oval, etc. A flat, rectangular-shaped medical device with a low profile may be desired when the medical device is designed to be implanted subcutaneously.

FIGS. 1 and 2 above described various examples of implantable medical devices. In some examples, a medical device system may include more than one medical device. For example, multiple medical devices 100/200 may be used cooperatively to detect and treat cardiac arrhythmias and/or other cardiac abnormalities. For example, multiple medical devices may be implanted in multiple chambers of the heart to provide multi-chamber therapy. Some example systems will be described below in connection with FIGS. 3-6. In such multiple device systems, it may be desirable to have the medical devices communicate with each other, or at least have some of the devices receive communication signals from other medical devices. Some example communication techniques are described below with respect to FIG. 3.

Figure 3:
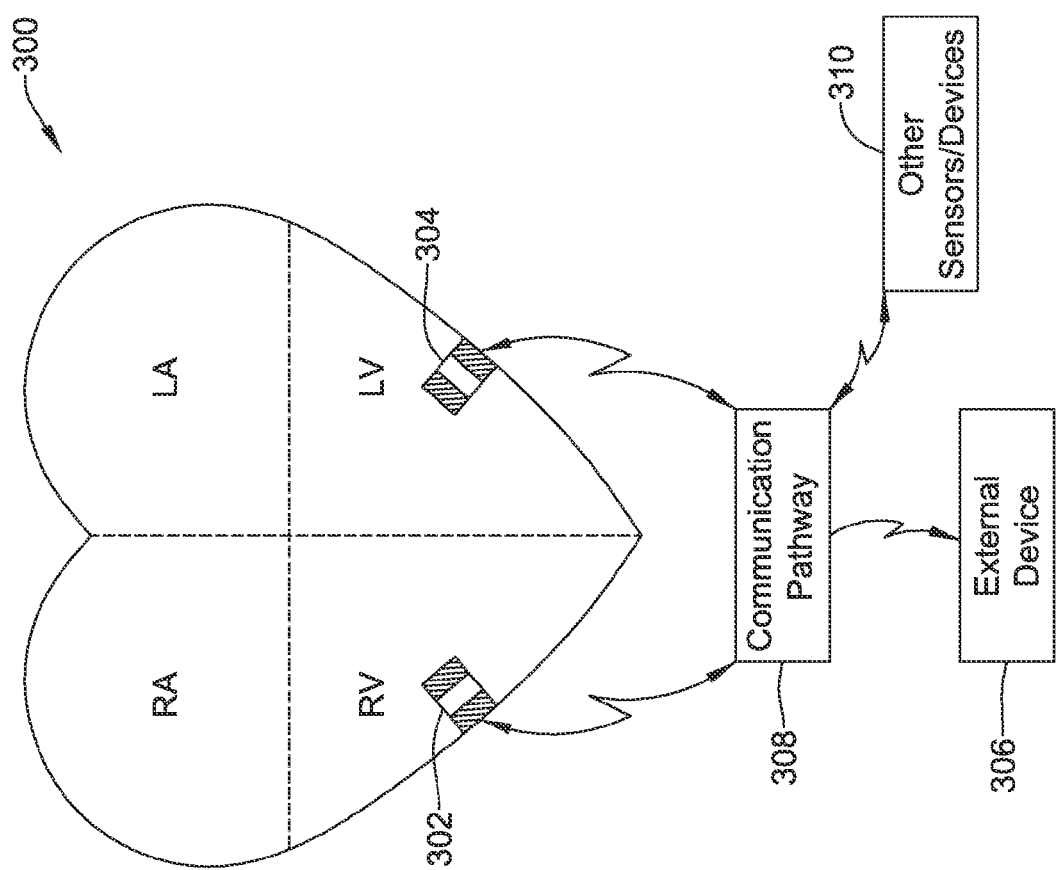
FIG. 3 is a schematic diagram of an exemplary medical system that includes multiple leadless cardiac pacemakers (LCPs) and/or other devices in communication with one another example of the present disclosure.

FIG. 3 illustrates an example of a medical device system and a communication pathway via which multiple medical devices may communicate. In the example shown, medical device system 300 may include LCPs 302 and 304, external medical device 306, and other sensors/devices 310. External device 306 may be any of the devices described previously with respect to MD 100, in addition to other medical devices such as implantable cardioverter-defibrillators (ICDs), diagnostic only medical devices, or other implanted or external (e.g. external to a patient's body) medical devices. Other sensors/devices 310 may also be any of the devices described previously with respect to MD 100 or other medical devices such as ICDs, diagnostic only devices, or other suitable medical devices. In other examples, other sensors/devices 310 may include a sensor, such as an accelerometer or blood pressure sensor, or the like. In still other examples, other sensors/devices 310 may include an external programmer device that may be used to program one or more devices of system 300.

Various devices of system 300 may communicate via communication pathway 308. For example, LCPs 302 and/or 304 may sense cardiac events and may communicate such signals to one or more other devices 302/304, 306, and 310 of system 300 via communication pathway 308. In one example, external device 306 may receive such signals and, based on the received signals, determine a heart rate and/or an occurrence of an arrhythmia. In some cases, external device 306 may communicate such determinations to one or more other devices 302/304, 306, and 310 of system 300. In other examples, LCPs 302 and 304 may determine heart rates or arrhythmias based on the communicated signals and may communicate such determinations to other communicatively coupled devices. Additionally, one or more other devices 302/304, 306, and 310 of system 300 may take action based on the communications, such as by delivering suitable electrical stimulation.

Communication pathway 308 may represent one or more of various communication methods. For example, the devices of system 300 may communicate with each other via RF signals, inductive coupling, optical signals, acoustic signals, or any other signals suitable for communication and communication pathway 308 may represent such signals. In at least one example, communicated pathway 308 may represent conducted communication signals. Accordingly, devices of system 300 may have components that allow for conducted communication. In examples where communication pathway 308 includes conducted communication signals, devices of system 300 may communicate with each other by sensing electrical communication pulses delivered into the patient's body by another device of system 300. The patient's body may conduct these electrical communication pulses to the other devices of system 300. In such examples, the delivered electrical communication pulses may differ from the electrical stimulation pulses of any of the above described electrical stimulation therapies. For example, the devices of system 300 may deliver such electrical communication pulses at a voltage level that is sub-threshold. That is, the voltage amplitude of the delivered electrical communication pulses may be low enough as to not capture the heart (e.g. not cause a contraction). Although, in some circumstances, one or more delivered electrical communication pulses may, deliberately or inadvertently, capture the heart, and in other circumstances, delivered electrical stimulation pulses may not capture the heart. In some cases, the delivered electrical communication pulses may be modulated (e.g. pulse width or amplitude modulated), or the timing of the delivery of the communication pulses may be modulated, to encode the communicated information. These are just some examples of how varying parameters of the communication pulse may convey information to another device. Other techniques may be used with such a conducted communication technique.

As mentioned above, some example systems may employ multiple devices for determining occurrences of arrhythmias and/or other heart conditions, and/or for delivering electrical stimulation. FIGS. 3-6 describe various example systems that may use multiple devices in order to determine occurrences of arrhythmias and/or other heart conditions, and/or deliver electrical stimulation therapy. However, FIGS. 3-6 should not be viewed as limiting examples. For example, FIGS. 3-6 describe how various multiple device systems may coordinate to detect various arrhythmias and/or other heart conditions, and/or deliver electrical stimulation therapy. However, any combinations of devices such as that described with respect to MD 100 and LCP 200, may used in concert with the below described techniques for detecting arrhythmias and/or other heart conditions, and/or delivering electrical stimulation therapy.

Figure 4:
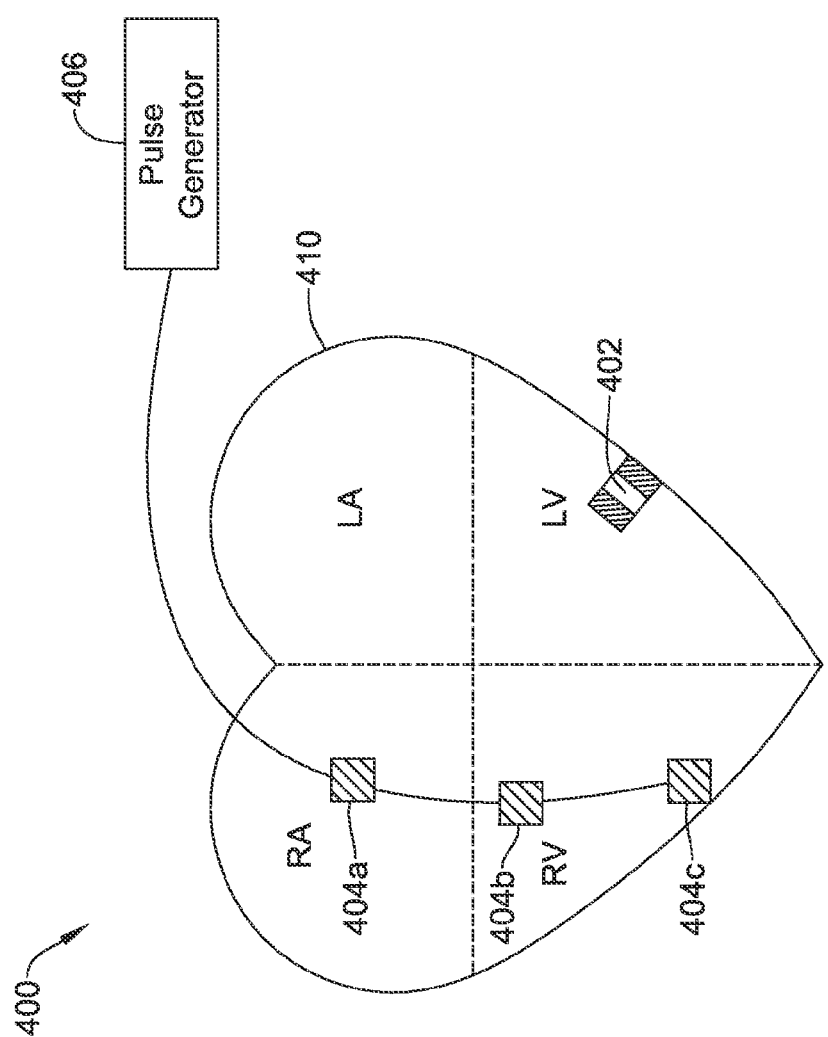
FIG. 4 is a schematic diagram of the a system including an LCP and another medical device, in accordance with another example of the present disclosure.

FIG. 4 illustrates an example medical device system 400 that includes an LCP 402 and a pulse generator 406. In this example, pulse generator 406 may be an implantable cardiac pacemaker (ICP). For example, pulse generator 406 may be an ICP such as that described previously with respect to MD 100. In examples where pulse generator 406 is an ICP, electrodes 404a, 404b, and 404c may be implanted on or within the right ventricle and/or right atrium of heart 410 via one or more leads. In other contemplated examples, pulse generator 406 may include electrodes implanted in the left ventricle and/or atrium of heart 410. These electrodes may instead be of or in addition to electrodes implanted within the right ventricle and/or atrium of heart 410. As shown, an LCP 402 may be implanted within heart 410. Although LCP 402 is depicted implanted within the left ventricle (LV) of the heart 410, in some instances, LCP 402 may be implanted within a different chamber of the heart 410. For example, LCP 402 may be implanted within the left atrium (LA) of heart 410 or the right atrium (RA) of heart 410. In other examples, LCP 502 may be implanted within the right ventricle (RV) of heart 410.

In any event, LCP 402 and pulse generator 406 may operate together to detect cardiac events and deliver electrical stimulation therapy. In some examples, devices 402 and 406 may operate independently to sense cardiac events of heart 410. For example, LCP 402 may sense cardiac events in the LV of heart 410 while pulse generator 406 may sense cardiac events in the RA and/or RV of heart 410. Either or both devices may optionally determine a contraction rate or occurrence of an arrhythmia based on the sensed cardiac events. In some examples, the contraction rate may be a rate of sensed cardiac events. That is, LCP 402 may determine a contraction rate for the LV of heart 410 while pulse generator 406 may determine a contraction rate for the RA and/or RV of heart 410. In some examples, devices 402 and 406 may determine occurrences of arrhythmias based at least in part on these determined contraction rates.

In some examples, devices 402 and 406 may additionally send and/or receive communication signals in order to more effectively deliver electrical stimulation to heart 410. For example, LCP 402 may send cardiac events sensed in the LV to pulse generator 406 and pulse generator 406 may send cardiac events sensed in the RA and/or RV to LCP 402. Devices 402 and 406 may additionally communicate any determined contraction rates to the other device. In some examples, devices 402 and 406 may optionally or additionally send other signals such as commands to perform various actions, for example to deliver electrical stimulation to heart 410. In some examples, communication may only occur in one direction. That is, only one of devices 402 and 406 may send communication signals to the other of devices 402 and 406. The receiving device may then make one or more determinations, such as contraction rate determinations or arrhythmia determinations, based on the received signals. Alternatively, the receiving device may perform one or more actions based on the received communication, for example delivering electrical stimulation.

Figure 5:
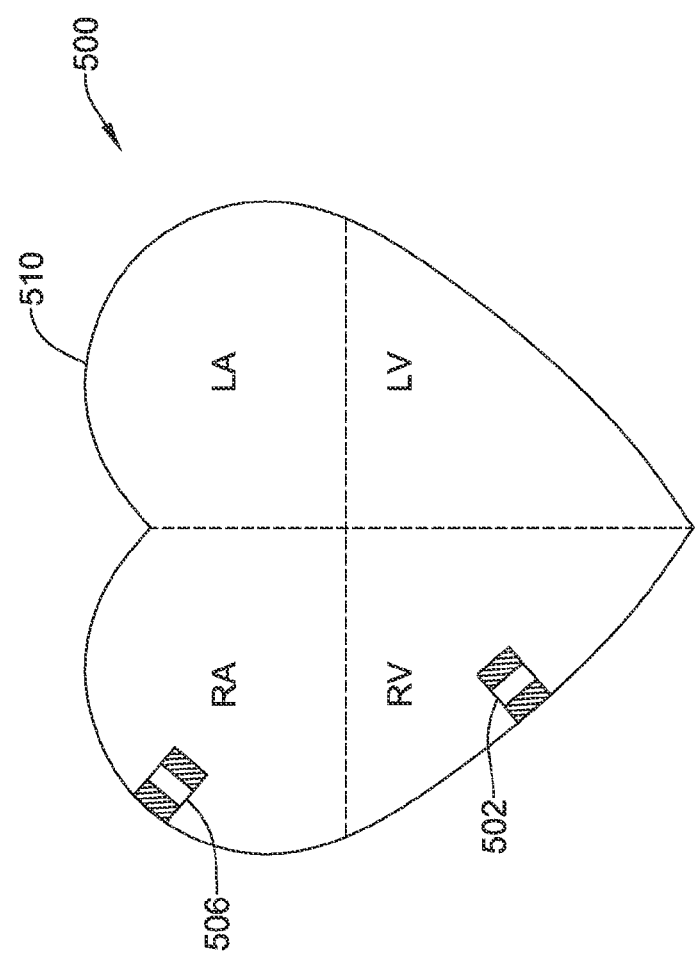
FIG. 5 is a schematic diagram illustrating a multiple leadless cardiac pacemaker (LCP) system in accordance with another example of the present disclosure.

FIG. 5 illustrates an example medical device system 500 that includes LCP 502 and LCP 506. LCP 502 and LCP 506 are shown implanted within a heart 510. Although LCPs 502 and 506 are depicted as implanted within the right ventricle (RV) of heart 510 and right atrium (RA) of heart 510, respectively, in other examples, LCPs 502 and 506 may be implanted within different chambers of heart 510. For example, system 500 may include LCPs 502 and 506 implanted within both atria of heart 510. In other examples, system 500 may include LCPs 502 and 506 implanted within both ventricles of heart 510. In more examples, system 500 may include LCPs 502 and 506 implanted within any combination of ventricles and atria. In yet other examples, system 500 may include LCPs 502 and 506 implanted within the same chamber of heart 510.

In any event, LCP 502 and LCP 506 may operate together to detect cardiac events and deliver electrical stimulation therapy. In some examples, devices 502 and 506 may operate independently to sense cardiac events of heart 510. For example, LCP 502 may sense cardiac events in the RV of heart 510 while LCP 506 may sense cardiac events in the RA of heart 510. Either or both devices may optionally determine a contraction rate or occurrence of an arrhythmia based on the sensed cardiac events. In some examples, the contraction rate may be a rate of sensed cardiac events. That is, LCP 502 may determine a contraction rate for the RV of heart 510 while LCP 506 may determine a contraction rate for the RA of heart 510. In some examples, devices 502 and 506 may determine occurrences of arrhythmias based at least in part on these determined contraction rates.

In some examples, devices 502 and 506 may additionally send and/or receive communication signals in order to more effectively deliver electrical stimulation to heart 510. For example, LCP 502 may send cardiac events sensed in the RV to LCP 506 and/or LCP 506 may send cardiac events sensed in the RA to LCP 502. Devices 502 and 506 may additionally communicate any determined contraction rates to the other device. In some examples, devices 502 and 506 may optionally or additionally send other signals such as commands to perform various actions, for example to deliver electrical stimulation to heart 510. In some examples, communication may only occur in one direction. That is, only one of devices 502 and 506 may send communication signals to the other of devices 502 and 506. The receiving device may then make one or more determinations, such as contraction rate determinations or arrhythmia determinations, based on the received signals. Alternatively, the receiving device may perform one or more actions based on the received communication, for example delivering electrical stimulation.

Figure 6:
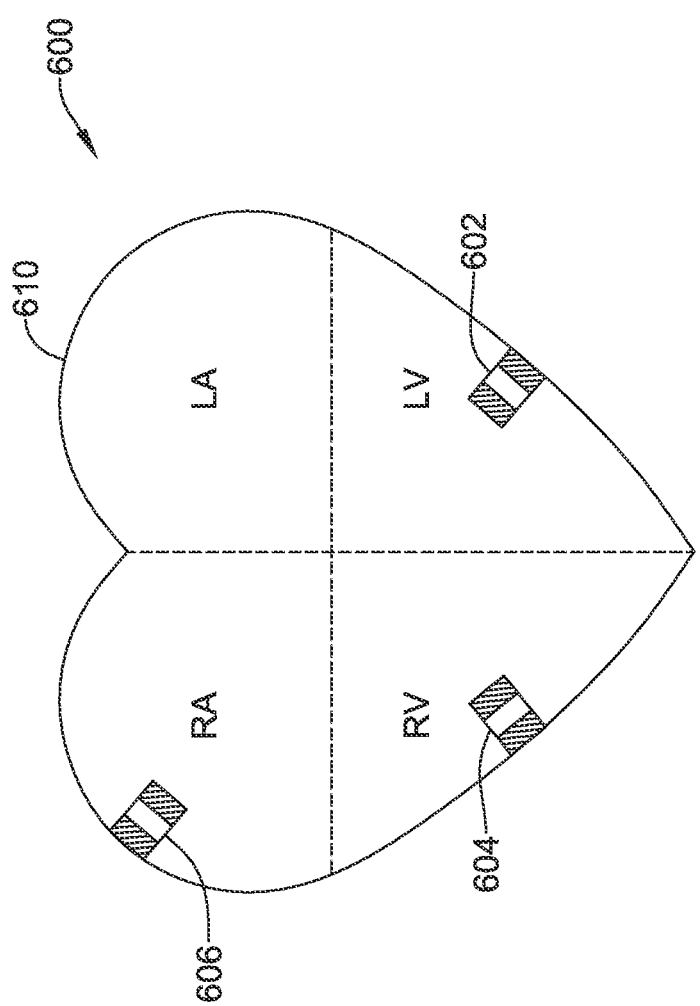
FIG. 6 is a schematic diagram illustrating a multiple leadless cardiac pacemaker (LCP) system, in accordance with yet another example of the present disclosure.

FIG. 6 illustrates an example medical device system 600 with three separate LCPs including LCP 602, LCP 604, and LCP 606. Although system 600 is depicted with LCPs 602, 604, and 606 implanted within the LV, RV, and RA, respectively, other examples may include LCPs 602, 604, and 606 implanted within different chambers of the heart 610. For example, system 600 may include LCPs implanted within both atria and one ventricle of the heart 610. In other examples, system 600 may include LCP 606 implanted within the LA of heart 610. More generally, it is contemplated that system 600 may include LCPs implanted within any combination of ventricles and atria. In some instances, system 600 may include two or more of LCPs 602, 604, and 606 implanted within the same chamber of the heart 610.

In any event, LCPs 602, 604, and 606 may operate together to detect cardiac events and deliver electrical stimulation therapy. In some examples, devices 602, 604, and 606 may operate independently to sense cardiac events of heart 610. For example, LCP 602 may sense cardiac events in the LV of heart 610, LCP 604 mays sense cardiac events in the RV of heart 610, and LCP 606 may sense cardiac events in the RA of heart 610. Any or all of devices 602, 604, and 606 may optionally determine a contraction rate or occurrence of an arrhythmia based on the sensed cardiac events. In some examples, the contraction rate may be a rate of sensed cardiac events. That is, LCP 602 may determine a contraction rate for the LV of heart 610, LCP 604 may determine a contraction rate for the RB of heart 610, and LCP 606 may determine a contraction rate for the RA of heart 610. In some examples, devices 602, 604, and 606 may determine occurrences of arrhythmias based at least in part on these determined contraction rates.

In some examples, devices 602, 604, and 606 may additionally send and/or receive communication signals in order to more effectively deliver electrical stimulation to heart 610. For example, LCP 602 may send cardiac events sensed in the LV to LCPs 604 and 606, LCP 604 may send cardiac events sensed in the RV to LCPs 602 and 606, and LCP 606 may send cardiac events sensed in the RA to LCPs 602 and 604. Devices 602, 604, and 606 may additionally communicate any determined contraction rates to the other devices. In some examples, devices 602, 604, and 606 may optionally or additionally send other signals such as commands to perform various actions, for example to deliver electrical stimulation to heart 610. In some examples, some of devices 602, 604, and 606 may only be configured to receive communication signals while others of devices 602, 604, and 606 may only be configured to send communication signals. For instance, only one or two of devices 602, 604, and 606 may be configured to send communication signals. Additionally in some examples, only one or two of devices 602, 604, and 606 may be configured to receive communication signals. In at least some examples, at least one of devices 602, 604, and 606 may be configured to both send and receive communication signals. Any of the receiving devices may then make one or more determinations, such as contraction rate determinations or arrhythmia determinations, based on the received signals. Alternatively, the receiving devices may perform one or more actions based on the received communication, for example delivering electrical stimulation.

The above described multi-device systems should not be construed as limiting the disclosed techniques to any particular multi-device configuration. As one example, one system may include two LCP devices and one ICP device. In other examples, some multi-device systems may include more than three devices, for instance systems may include four LCP devices or three LCP devices and an ICP device. Even the spatial positions of the LCPS and/or electrodes of the ICP as depicted in FIG. 3-6 are merely exemplary. For example, the LCPs may not reside within the chambers of the heart. Rather, in some examples, one or more of the LCPs may reside on an epicardial surface of the heart proximate a chamber of the heart. The electrodes of the ICP may vary in number and/or may span more or fewer chambers in some examples. Accordingly, many variations of the depicted multi-device systems are contemplated that may implement the disclosed sensing, treatment, and communication techniques described herein.

Figure 7:
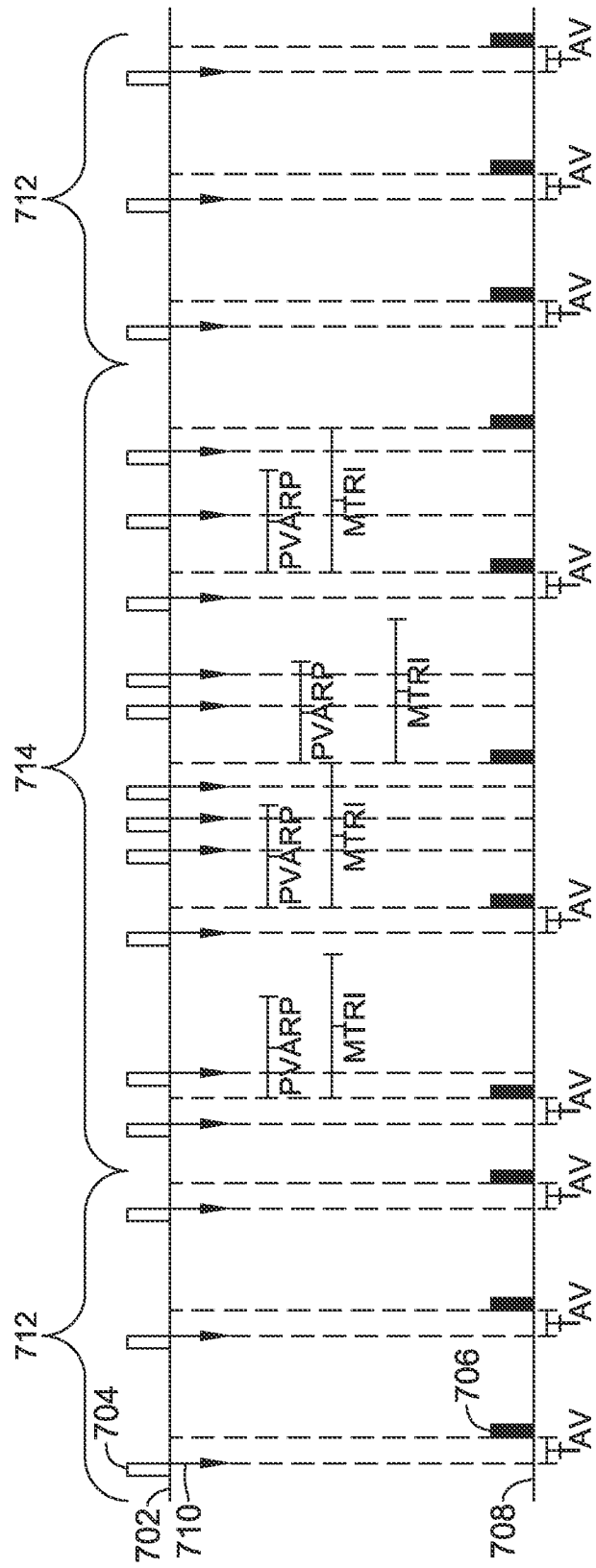
FIG. 7 is a graphical depiction of sensed and paced cardiac events showing an illustrative method of multi-chamber therapy in accordance with the present disclosure.

FIG. 7 is a graphical depiction of sensed and paced cardiac events showing an illustrative method of multi-chamber therapy in accordance with the present disclosure. In a multi-chamber therapy, a ventricle may be paced based on a contraction of an atrium. This coordination of contractions between the atrium and the corresponding ventricle may allow for some physiological benefits in comparison to un-coordinated or un-synchronized contractions of the atria and the ventricles. However, merely tracking the contraction of the ventricle with the contraction of the atrium may result in an undesirable heart rate if appropriate safeguards are not considered.

FIG. 7 shows time lines 702 and 708 that show sensed and paced cardiac events for an atrium and a ventricle, respectively, for a multi-device system that implements multi-chamber therapy. Such a system may have a first device that is responsible for sensing cardiac events in and delivering electrical stimulation to a ventricle of the heart. The system may also include a second device that is responsible for at least sensing cardiac events in, and additionally in some examples delivering electrical stimulation to, an atrium of the heart. Line 702 depicts sensed and paced atrial events, and line 708 depicts sensed and paced ventricular events. Sensed cardiac events are cardiac events, such as contractions, that are caused by intrinsically generated cardiac electrical signals and which are sensed by the first or second devices. Paced cardiac events are cardiac events that are caused by a delivery of electrical stimulation, such as by the first or second devices. In FIG. 7, open bars represent sensed cardiac events, for example, sensed atrial events 704, and closed bars represent paced cardiac events, such as paced ventricular events 706.

In the example of FIG. 7, in regions 712, the atrium of the heart is shown operating in a normal fashion by beating at a safe, acceptable contraction rate. In this example, the second device 506 of a multi-device system that is implementing a multi-chamber therapy may communicate sensed atrial events 704 to the first device which may be located in the ventricle. Communication of sensed atrial events 704 is represented by arrows 710. In the example shown, each arrow 710 may represent a communication of a sensed atrial event 704 by the second device to the first device. The second device may communicate sensed atrial events 704 to the first device, for example, by sending a communication pulse. In some examples the second device may select various features of the communication pulse in order to communicate sensed atrial events 704. For example, the second device may select a monophasic, biphasic, pulse width, pulse amplitude, or other pulse morphology feature in order to communicate sensed atrial events 704. In other examples, the second device may send a string of communication pulses that communicate sensed atrial events 704. The first device may be configured to deliver a pacing pulse in order to stimulate the ventricle of the heart into contracting in response to receiving a communicated sensed atrial event 704. For example, in regions 712 of FIG. 7, the communicated sensed atrial events 704 are followed by paced ventricular events 706 occurring a set time after the communicated sensed atrial events 704. In such a system, the first device may be configured to wait a predetermined amount of time, sometimes termed an atrioventricular delay and represented by $T_{AV}$ in FIG. 7, before delivering a pacing pulse in response to receiving a sensed atrial event 704 from the second device.

Regions 712 depict how the first and second devices may operate in a "tracking mode", where the first device "tracks" the second device, for example, by delivering pacing pulses in response to each received sensed atrial event 704 from the second device. However, merely tracking each sensed atrial event 704 and stimulating the ventricle to contract in response to each sensed atrial event 704 can cause problems if the rate of sensed atrial events 704 becomes too high (or too low).

Regions 714 depict a period of a high rate of atrial beating, for example during an atrial fibrillation event. In such instances, it may be unsafe to attempt to cause the ventricle to contract at a similarly high rate. Accordingly, such multi-chamber therapy systems may have one or more safeguards in order to mitigate such potentially dangerous conditions. One safeguard that may be employed by the first device is to have a maximum tracking rate interval (MTRI). An MTRI is a predefined period of time that must pass from the most recently delivered pacing pulse or sensed ventricular event by the first device before the first device may deliver another pacing pulse. Another safeguard may include a post ventricular atrial refractory period (PVARP). A PVARP may be a predefined period of time immediately following a sensed or paced atrial event. During this PVARP, the first device may be configured to ignore any communicated sensed atrial events 704. That is, the first device may not deliver electrical stimulation in response to any communicated sensed atrial events 704 during this time period. One difference between the MTRI and PVARP is that, if the first device receives a communicated sensed atrial event 704 after the PVARP period but before the MTRI, the first device may deliver a pacing pulse as soon as the MTRI ends. However, if the first device receives one or more communicated sensed atrial events 704 during the PVARP, but none after the PVARP and before the MTRI, the first device may not deliver a pacing pulse as soon as the PVARP ends. The PVARP may be reset after the first device delivers a pacing pulse. These various features are depicted in region 714 of FIG. 7. In this manner, the first device may be configured to cause the ventricle of the heart to contract no faster than a predefined rate that is controlled by an MTRI period and/or a PVARP.

Figure 8:
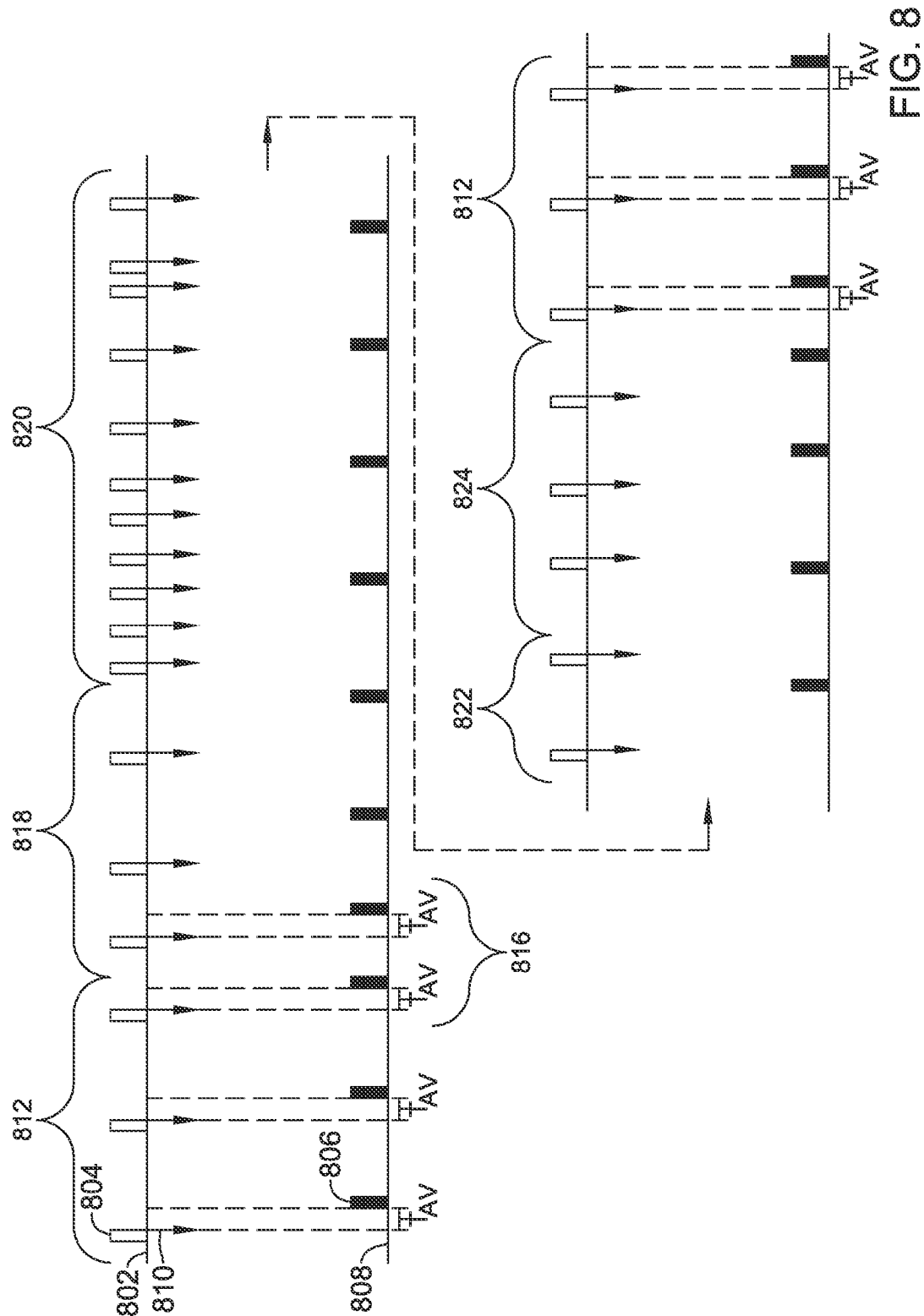
FIG. 8 is a graphical depiction of cardiac events showing another illustrative method of multi-chamber therapy in accordance with the present disclosure.
Figure 9:
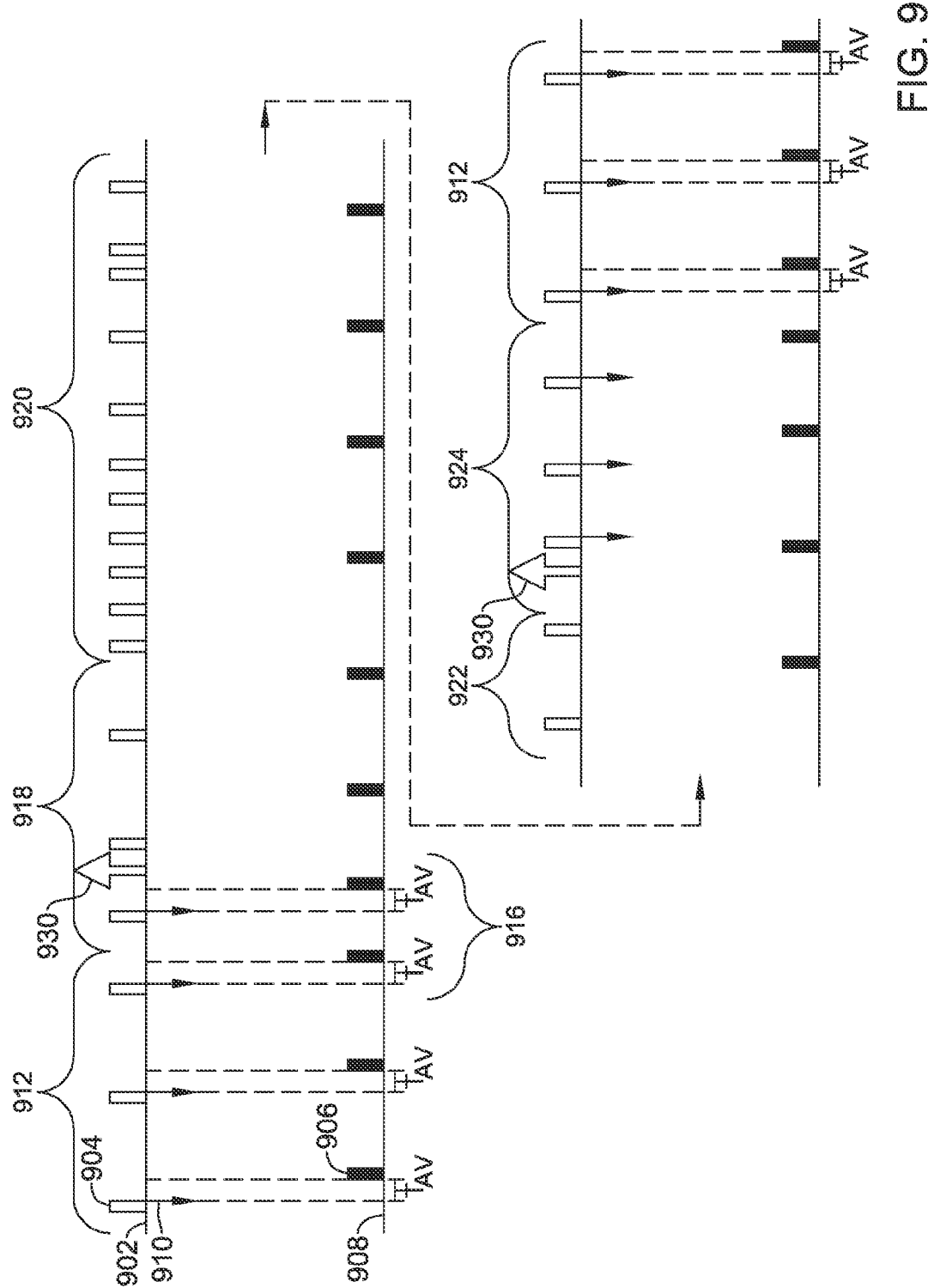
FIG. 9 is a graphical depiction of cardiac events showing another illustrative method of multi-chamber therapy in accordance with the present disclosure.
Figure 10:
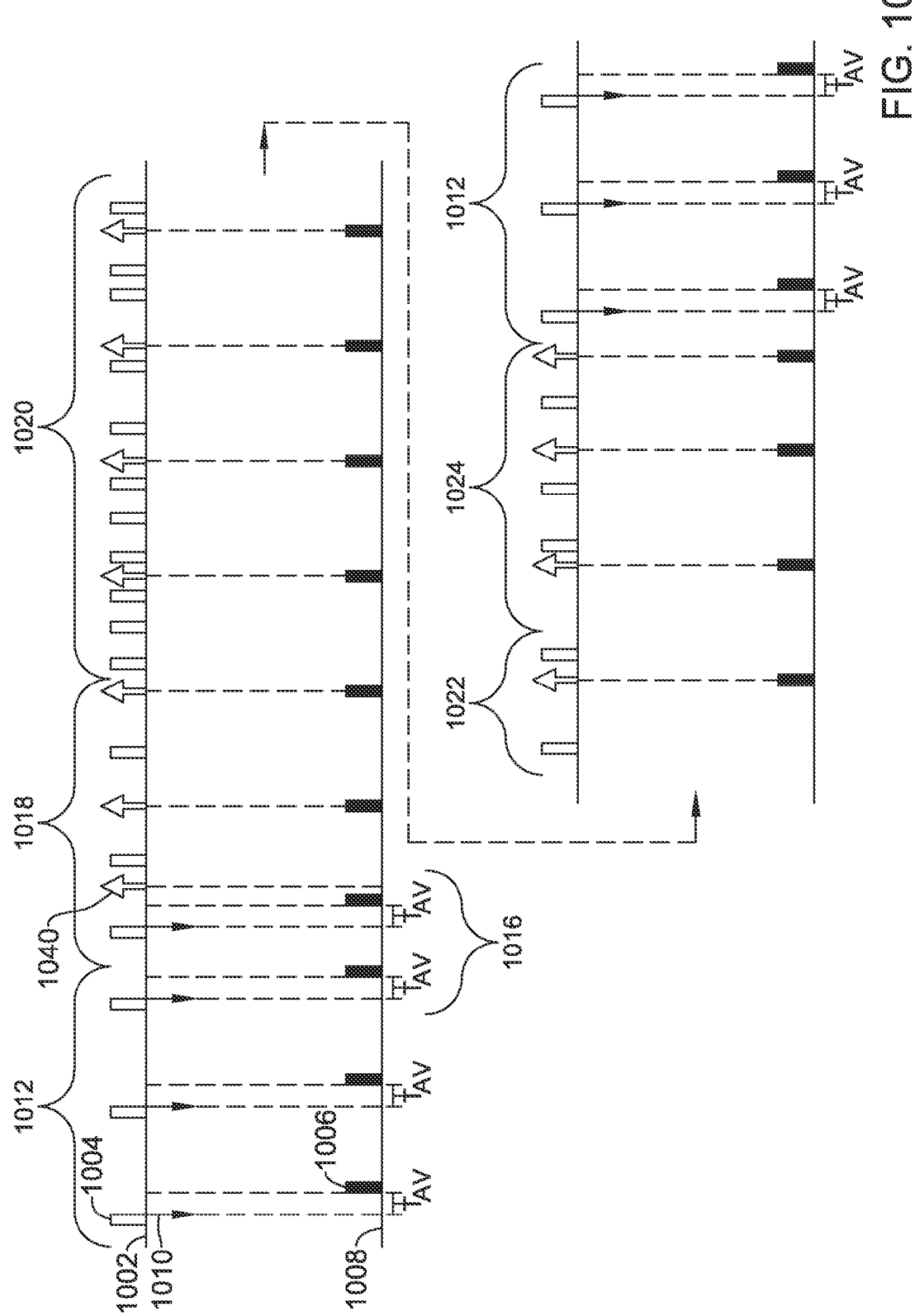
FIG. 10 is a graphical depiction of cardiac events showing another illustrative method of multi-chamber therapy in accordance with the present disclosure.

Although FIG. 7 was described with respect to a multi-device system, the described implementation of the multi-chamber therapy may be applied by single device systems. For example, a system comprising a single device could simply implement the various PVARP and/or MTRI periods and do away with communicating sensed atrial events 704 between devices, as the singular device would have access to both sensed atrial events 704 and the ability to deliver electrical stimulation in response to sensed atrial events 704. FIGS. 8-10, on the other hand, represent multi-chamber therapies that multi-device systems may implement which control the coordination of contractions between the atria and the ventricles based on communication between the devices.

FIG. 8 depicts another multi-chamber therapy that a multi-device system may implement. Such a system may have a first device that is responsible for sensing cardiac events in and delivering electrical stimulation to a ventricle of the heart. The system may further comprise a second device that is responsible for at least sensing cardiac events in, and additionally in some examples delivering electrical stimulation to, an atrium of the heart. Similar to FIG. 7, time lines 802 and 808 depict sensed and paced atrial and ventricular events, respectively. Also, sensed atrial events 804 are atrial cardiac events sensed by the second device and paced ventricular events 806 are paced ventricular paced events caused by the first device. Arrows 810 represent communicated sensed atrial events 804. The second device may be configured to communicate sensed atrial events 804 in a manner similar to one or more of the examples described above with respect to FIG. 7. Again, similarly to FIG. 7, regions 812 of FIG. 8 represent periods of normal atrial activity. During these periods, the second device may communicate sensed atrial events 804 to the first device, and the first device may deliver electrical stimulation, for example pacing pulses, after a predefined time period $T_{AV}$ from receiving a communicated sensed atrial event 804 in a "tracking mode".

As described previously with respect to FIGS. 3-6, one or more of the first and second devices may determine a contraction rate, for instance an atrial contraction rate. In at least some examples, the first device may determine a contraction rate based on communicated sensed atrial events 804. In some examples, the first device may determine a contraction rate based on the two most previous communicated sensed atrial events 804. In other examples, the first device may determine a contraction rate based on a different number of the most recent communicated sensed atrial events 804, such as three, five, ten, or any other suitable number of sensed atrial events 804. The first device may additionally compare the determined contraction rate to a threshold. If the first device determines that the atrial contraction rate is above the threshold, the first device may switch into a different mode. Region 816 of FIG. 8 may represent a period when the first device determines that the contraction rate is above a threshold. Additionally or in other examples, the first device may track an interval between consecutive atrial events. The first device may then compare the interval to a threshold and when the interval becomes shorter than a threshold duration, the first device may switch into a different mode. In such examples, the first device may monitor an interval between two, three, five, ten, or any other suitable number of atrial events in order to determine whether the interval is less than the threshold duration. In at least some examples, the first device may be configured to monitor an interval between each pair of consecutive atrial events and to average two or more of the intervals to produce a composite interval before determining whether the composite interval becomes shorter than the threshold duration. In other examples, the first device may be configured to monitor the interval between each pair of consecutive atrial events and count the intervals that are shorter than a threshold duration within a predetermined duration, for example 5 seconds, 7 seconds, or 10 seconds, or any other suitable duration. In such examples, the first device may be configured to switch to a different mode when a predetermined total number of intervals, for example 2 intervals, 5 intervals, 8 intervals, or any other suitable number of intervals, within the predetermined duration exceeds a threshold.

After determining that a contraction rate is above a threshold, the first device may switch from a tracking mode to an atrial tachycardia (ATR) mode. During the ATR mode, the first device may cease delivering electrical stimulation in response to receiving sensed atrial events 804. Rather, the first device may switch to delivering electrical stimulation at a predefined rate. This predefined rate may be a safe contraction rate for the heart. In some examples, this predefined rate may be programmable by a user of an external programming device when in communication with the second device (e.g. at the time of implantation or during a programming session). In some examples, this predefined rate may be equal to a lower rate limit (LRL) which is a minimum safe rate for contraction of the ventricle. Region 820 of FIG. 8 may represent a time when the first device is operating in an ATR mode. Optionally or additionally in some examples, rather than immediately beginning to deliver electrical stimulation at the predefined rate after switching to the ATR mode, the first device may lower the rate of delivered electrical stimulation slowly over a period of time, for example seconds, minutes, or hours, down to the predefined rate. Region 818 represents a time when the first device is lowering the rate of delivered electrical stimulation down to the predetermined rate.

In some examples, the second device continues to communicate sensed atrial events 804. In ATR mode, the first device may ignore any received sensed atrial events 804 for purposes of delivering electrical stimulation. However, even during ATR mode, the first device may continue to determine a contraction rate from the received sensed atrial events 804 and compare the determined contraction rate to the threshold. Once the first device determines that the atrial contraction rate has fallen back below the threshold, the first device may switch back to the tracking mode and begin to deliver electrical stimulation in response to received sensed atrial events 804 from the second device, as in regions 812 of FIG. 8. In some examples, the first device may slowly increase the rate of delivered electrical stimulation up to the rate at which the first device is receiving sensed atrial events 804 before switching back to the tracking mode, as can be seen in region 824 of FIG. 8.

FIG. 9 is another example of a multi-chamber therapy technique for use in a multi-device system. As with the previous examples, such a system may have a first device that is responsible for sensing cardiac events in and delivering electrical stimulation to a ventricle of the heart. The system may further include a second device that is responsible for at least sensing cardiac events in, and additionally in some examples delivering electrical stimulation to, an atrium of the heart. Time lines 902 and 908 of FIG. 9 depict sensed and paced atrial and ventricular events, respectively. Also, sensed atrial events 904 are atrial cardiac events sensed by the second device, and paced ventricular events 906 are paced ventricular paced events caused by the first device. Arrows 910 represent communicated sensed atrial events 904. The second device may be configured to communicate sensed atrial events 904 in a manner similar to one or more of the examples described above with respect to FIG. 7. Similar to FIGS. 7 and 8, regions 912 of FIG. 9 represent periods of normal atrial activity. During these periods, the second device may communicate sensed atrial events 904 to the first device, and the first device may deliver electrical stimulation, for example pacing pulses, after a predefined time period $T_{AV}$ from receiving a communicated sensed atrial event 904 in a tracking mode.

In the example of FIG. 9, the second device may determine a contraction rate from sensed atrial events 904, and/or by monitoring an interval between consecutive atrial events, for instance in a manner similar to one of the examples described with respect to FIG. 8. The second device may additionally compare the determined contraction rate to a threshold and/or the monitored interval to a threshold duration. Once the second device determines that the contraction rate exceeds a threshold, or the interval becomes shorter than the threshold duration, for example during region 916 of FIG. 9, the second device may communicate a mode switch signal 930 to the first device. The mode switch signal 930 may cause the first device to switch from a "tracking mode" as described above to an ATR mode. Accordingly, the first device may begin delivering electrical stimulation according to an ATR therapy protocol. In some examples, the ATR therapy protocol may cause the first medical device to deliver electrical stimulation at a predefined rate. Region 920 of FIG. 9 represents a period of time when the first device is operating in ATR mode executing an ATR therapy protocol. As depicted in region 920, the delivered pacing pulses are not correlated with sensed atrial events 904. The predefined rate may be a safe contraction rate for the heart. In some examples, this predefined rate may be programmable by a user of an external programming device when in communication with the first and/or second device (e.g. at the time of implantation or during a programming session). In some examples, this predefined rate may be equal to a lower rate limit (LRL), which may be a desired minimum safe rate for contraction of the ventricle. Optionally or additionally in some examples, rather than immediately beginning to deliver electrical stimulation at the predefined rate after switching to the ATR mode, the first device may lower the rate of delivered electrical stimulation slowly over a period of time, for example seconds, minutes, or hours, down to the predefined rate. This transition is depicted in region 918 of FIG. 9.

In some examples, the second device continues to determine the contraction rate based on sensed atrial events 904. However, unlike the techniques described in FIG. 8, after communicating the mode switch signal 930, which caused the first device to switch from a tracking mode to an ATR mode, the second device may cease communicating sensed atrial events 904 to the first device. This can be seen by the absence of arrows 910 in regions 918, 920, and 922 of FIG. 9. Once the second device determines that the contraction rate has fallen back below the threshold, the second device may communicate another mode switch signal 930 to the first device. This second communicated mode switch signal 930 may cause the first device to switch back from the ATR mode to the tracking mode. After communicating the second mode switch signal 930 to the first device, the second device may start again to communicate sensed atrial events 904 so that the first device can deliver electrical stimulation in response to received sensed atrial events 904 in the tracking mode. In some examples, the first device may slowly increase the rate of delivered electrical stimulation up to the rate at which the first device is receiving sensed atrial events 804 before beginning to deliver electrical stimulation based on received sensed atrial events 904. This slow increase in rate can be seen in region 924 of FIG. 9, where the rate of delivered pacing pulses is still disconnected from the received sensed atrial events 904, but is increasing. In such examples, once the rate of delivered pacing pulses has increased a certain amount relative to the heart rate, the first device may then begin delivering pacing pulses based on received sensed atrial events 904, as seen in regions 912.

FIG. 10 is yet another example of a multi-chamber therapy technique for use in a multi-device system. As with the previous examples, such a system may have a first device that is responsible for sensing cardiac events in and delivering electrical stimulation to a ventricle of the heart. The system may further comprise a second device that is responsible for at least sensing cardiac events in, and additionally in some examples delivering electrical stimulation to, an atrium of the heart. Time lines 1002 and 1008 of FIG. 10 depict sensed and paced atrial and ventricular events, respectively. Also, sensed atrial events 1004 are atrial cardiac events sensed by the second device and paced ventricular events 1006 are paced ventricular paced events caused by the first device. Arrows 1010 represent communicated sensed atrial events 1004. The second device may be configured to communicate sensed atrial events 1004 in a manner similar to one or more of the examples described above with respect to FIG. 7. Similar to FIGS. 7-9, regions 1012 of FIG. 10 represents periods of normal atrial activity. During these periods, the second device may communicate sensed atrial events 1004 to the first device, and the first device may deliver electrical stimulation, for example pacing pulses, after a predefined time period $T_{AV}$ from receiving a communicated sensed atrial event 1004.

In the example of FIG. 10, the second device may determine a contraction rate from sensed atrial events 1004, and/or monitor an interval between consecutive atrial events, for instance in a manner similar to one of the examples described with respect to FIG. 8. The second device may additionally compare the determined contraction rate to a threshold and/or the monitored interval to a threshold duration. Once the second device determines that the heart rate exceeds a threshold, or the monitored interval becomes shorter than the threshold duration, for example during region 1016 of FIG. 10, the second device may enter an ATR mode. During this mode, the second device may communicate artificial sensed events to the first device, represented by artificial sensed events 1040, instead of communicating sensed atrial events 1004. In at least some examples, the second device additionally may communicate a signal to the first device that the second device is entering ATR mode, e.g. switching from a tracking mode to an ATR mode.

In ATR mode, the second device may communicate artificial sensed events 1040 at a predefined rate, which may be a safe contraction rate for the heart. This can be seen in regions 1018, 1020, 1022, and 1024 of FIG. 10 represented by the lack of arrows 1010 and the addition of communicated artificial sensed events 1040. In some examples, the predefined rate may be equal to a lower rate limit (LRL) which is a desired minimum safe rate for contraction of the ventricle. Optionally or additionally in some examples, rather than immediately communicating artificial sensed paced events at the predefined rate after switching to the ATR mode, the second device may communicate artificial sensed paced events 1040 at continually lower rates down to the predefined rate. This feature can be seen in region 1018, where the rate of communicated artificial sensed events 1040 slowly reduces down to the predefined rate, and remains at the predefined rate during region 1020 of FIG. 10.

In some examples, the second device may communicate a mixture of artificial sensed events 1040 and sensed atrial events 1004. For example, the second device may track a first predefined period of time from the last communicated sensed event, e.g. either a sensed atrial event 1004 or an artificial sensed event 1040. The second device may be configured to not communicate any sensed atrial events 1004 sensed during the first predefined time period. If the second device senses an atrial event within a second predefined time period following the first predefined time period, the second device may communicate the sensed atrial event 1004 and reset the timer for tracking the first predefined period of time. However, if the second device does not sense any atrial events during the second predefined time period, the second device may then communicate an artificial sensed atrial event 1040 at the end of the second predefined time period.

In some examples, the second device continues to determine a contraction rate based on sensed atrial events 1004, even during the first and/or second predefined time periods. Once the second device determines that the contraction rate has fallen back below the threshold, such as during region 1022 of FIG. 10, the second device may switch out of the ATR mode and back to the tracking mode. After switching out of the ATR mode, the second device may start again to communicate every sensed atrial event. In some examples, the second device may slowly increase the rate of communicated sensed atrial events 1004, for example by still communicating some artificial sensed events 1040, up to the actual rate of sensed atrial events 1004. This feature can be seen in region 1024 of FIG. 10, where the second device communicates artificial sensed events 1040 at an increasing rate. Once the rate of communicated artificial sensed events 1040 increase by a certain amount relative to the contraction rate, the second device may then begin communicating only sensed atrial events 1004, such as during regions 1012 of FIG. 10. This may cause the contraction rate at which the first device delivers electrical stimulation to slowly increase as well.

Figure 11:
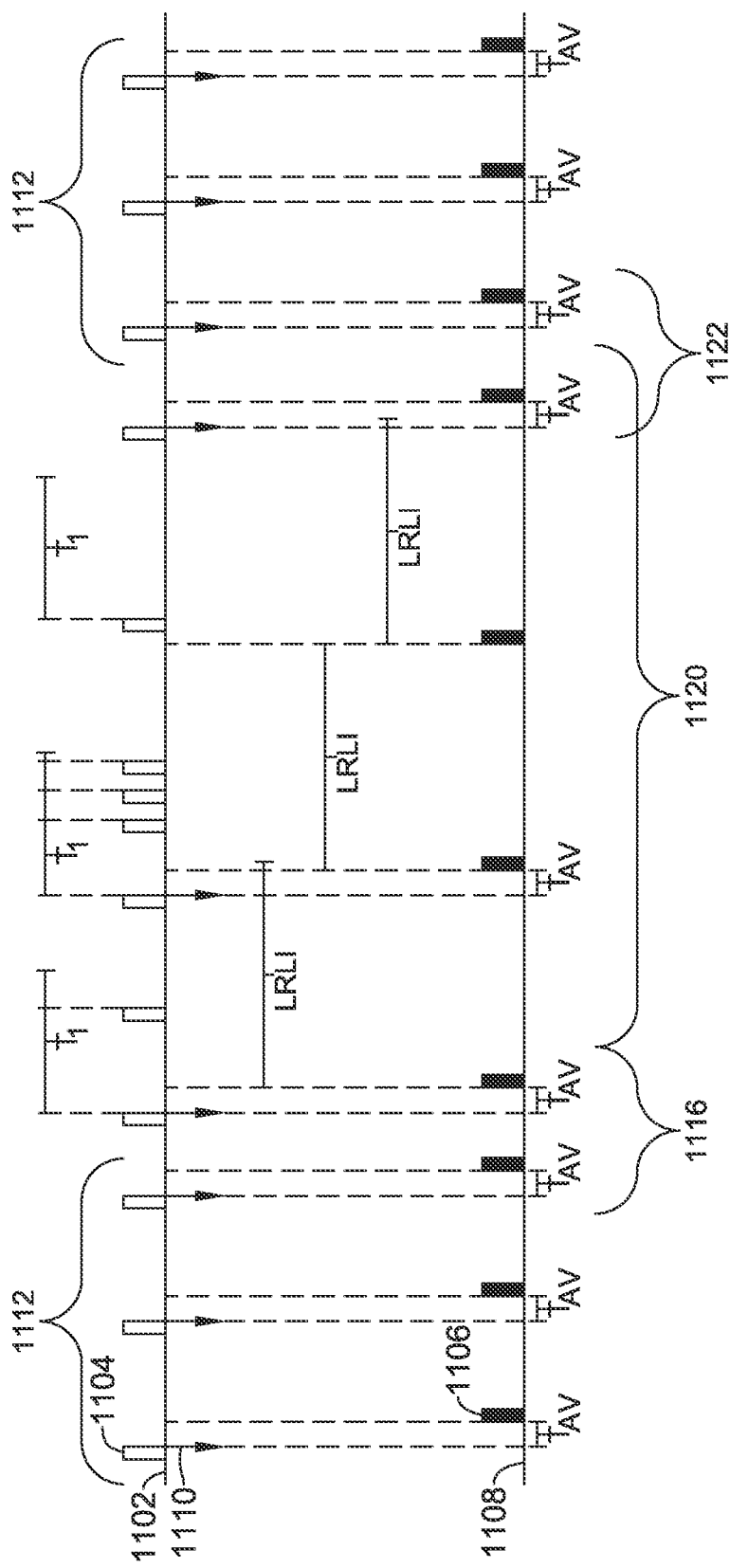
FIG. 11 is a graphical depiction of cardiac events showing another illustrative method of multi-chamber therapy in accordance with the present disclosure.

FIG. 11 is a graphical depiction of cardiac events showing another illustrative method of multi-chamber therapy in accordance with the present disclosure. As with the previous examples, such a system may have a first device that is responsible for sensing cardiac events in and delivering electrical stimulation to a ventricle of the heart. The system may further comprise a second device that is responsible for at least sensing cardiac events in, and additionally in some examples delivering electrical stimulation to, an atrium of the heart. Time lines 1102 and 1108 of FIG. 11 depict sensed and paced atrial and ventricular events, respectively. Also, sensed atrial events 1104 are atrial cardiac events sensed by the second device, and paced ventricular events 1106 are paced ventricular paced events caused by the first device. Arrows 1110 represent communicated sensed atrial events 1104. The second device may be configured to communicate sensed atrial events 1104 in a manner similar to one or more of the examples described above with respect to FIG. 7. Similar to FIGS. 7-10, regions 1112 of FIG. 11 represent a period of normal atrial activity. During these periods, the second device may communicate sensed atrial events 1104 to the first device, and the first device may deliver electrical stimulation, for example pacing pulses, after a predefined time period $T_{AV}$ from receiving a communicated sensed atrial event 1104 in a tracking mode.

In the example of FIG. 11, the second device may determine a contraction rate from sensed atrial events 1104, and/or monitor an interval between consecutive atrial events, for instance in a manner similar to one of the examples described with respect to FIG. 8. The second device may additionally compare the determined contraction rate to a threshold and/or the monitored interval to a threshold duration. Once the second device determines that the contraction rate exceeds a threshold, or the interval becomes shorter than the threshold duration, such as during region 1116 of FIG. 11, the second device may enter an ATR mode and only communicate selective sensed atrial events 1104.

In the ATR mode, the second device may use a blanking period, termed $T_1$ in FIG. 11, following each communicated sensed atrial event 1104. During this blanking period, the second device may not communicate any sensed atrial events 1104. The second device may then communicate the first sensed atrial event 1104 that occurs after the blanking period. This can be seen by the first two sensed atrial events 1104 of region 1120 of FIG. 11. The first sensed atrial event 1104 of region 1120 occurs before the end of a period of time $T_1$. Accordingly, the second device does not communicate that sensed atrial event 1104. The second atrial event 1104 of region 1120, however, does occur after a period of time $T_1$. Accordingly, the second device does communicate that sensed atrial event 1104, and the first device delivers a pacing pulse in response to receiving the communicated sensed atrial event 1104. By selectively communicating such sensed atrial events 1104, the second device may be able to prevent the first device from delivering electrical stimulation at an unsafe contraction rate.

In at least some examples, the first device keep track of a second predefined period of time. The first device may track the second predefined period of time from each paced ventricular event 1106. The first device may be configured to deliver a pacing pulse after the expiration of the second predefined period of time since. This period of time may be termed a lower rate limit interval (LRLI), as seen in FIG. 11 in region 1120. After the second paced ventricular event 1106 of region 1120, there are no sensed atrial events 1104 that fall outside of $T_1$ and before the LRLI. Accordingly, since the full LRLI period has run since the last paced ventricular event 1106, the first device delivers a pacing pulse triggering a paced ventricular event 1106, i.e. the third paced ventricular event 1106 of region 1120. In some examples, the second device may be able to sense when the first device delivers electrical stimulation that is not in response to a communicated sensed atrial event 1104. In such examples, when the second device senses such delivered electrical stimulation, the second device may reset the blanking period $T_1$. In other examples, the second device may begin tracking time for $T_1$ after sensing any delivered electrical stimulation by the first device instead of measuring the time from the last sensed atrial event 1104. For example, the second device may measure the blanking period $T_1$ from each paced ventricular event 1106 rather than from each communicated sensed atrial event 1104.

Even while only selectively communicating sensed atrial events 1104, the second device may determine the contraction rate. Once the second device determines that the contraction rate rises above the threshold, such as during region 1122 of FIG. 11, the second device may revert back to the tracking mode and may communicate each sensed atrial event 1104, as in regions 1112.

Although described mainly with respect to FIG. 7, any or all of the various examples described in FIGS. 8-11 may additionally or optionally employ the PVARP and MTRI periods described in FIG. 7. For example, when used, any of the first or second devices of any of the above described examples may ignore atrial events sensed or communicated during a PVARP. Additionally, when used, any of the first or second devices of any of the above described examples may use an MTRI to ensure that sensed atrial events are not communicated, or ventricular pacing pulses are not delivered, at a rate faster than that limited by the MTRI.

Additionally, any of the above described examples may additionally or optionally implement an LRLI as described with respect to FIG. 11. For example, the first device of any of the above examples may be configured to deliver a pacing pulse after the expiration of an LRLI period, measured from the last sensed ventricular event or paced ventricular event. Such a feature operates to set a minimum rate at which the heart contracts, thereby helping to ensure the safety of the patient. For example, such a feature may be beneficial in systems where the second device, as described above with respect to FIG. 7-11, controls the operation of the first device. In some of the described examples, the first device may deliver pacing pulses in response to signals communicated from the second device. However, in situations where communication between the two devices fails, the first device may still deliver pacing pulses at a safe rate based on an implemented LRLI period.

FIG. 12 is a flow diagram of an illustrative method that may be implemented by an implantable medical device system such as shown in any of FIGS. 3-6 including any of the devices described with respect to FIGS. 1 and 2. Although the method of FIG. 12 is described with respect to the medical device system of FIG. 5, the method of FIG. 12 may be performed by any suitable medical device system.

In some examples, LCP 506 may sense two or more atrial events (1202). For example, LCP 506 may be implanted in an atrium of heart 510 and may be configured to sense atrial events. LCP 506 may additionally be configured to determine an atrial interval between successive atrial events (1204). For example, LCP 506 may be configured to monitor a period of time between successive atrial events. In some examples, LCP 506 may be configured to monitor periods of time between two successive atrial events. In other examples, LCP 506 may be configured to monitor periods of time between three, five, ten, or any suitable number of atrial events. LCP 506 may be configured to determine a single atrial interval based on the monitored periods of time, for example by averaging the monitored periods of time. LCP 506 may further be configured to determine whether the atrial interval indicates an atrial contraction rate that is above a threshold (1206). For example, LCP 506 may be configured to compare the determined atrial interval to a threshold. In some examples, LCP 506 may determine an atrial contraction rate based on the determined atrial interval. In such examples, LCP 506 may compare the determined atrial contraction rate to the threshold.

If LCP 506 determines that the atrial contraction rate is below the threshold, LCP 506 may communicate the sensed atrial events from to LCP 502, wherein LCP 502 is configured to pace a ventricle of the heart in response to the communicated events in a tracking mode (1208). In the tracking mode, LCP 502, implanted within or on a ventricle of heart 510, may be configured to deliver a pacing pulse to the ventricle of heart 510 in response to each received sensed atrial event. However, if LCP 506 determines that the atrial contraction rate is above the threshold, LCP 506 may communicate to LCP 502 a command to pace the ventricle of the heart in a non-tracking mode (1210). In the non-tracking mode, LCP 502 may be configured to deliver pacing pulses to the ventricle of heart 510 according to any of the non-tracking modes described previously with respect to FIGS. 7-11, for instance an ATR mode and/or in any other suitable mode as desired.

FIG. 13 is a flow diagram of an illustrative method that may be implemented by an implantable medical device system such as shown in any of FIGS. 3-6 including any of the devices described with respect to FIGS. 1 and 2. Although the method of FIG. 13 will be described with respect to the medical device system of FIG. 5, the method of FIG. 13 may be performed by any suitable medical device system.

In some examples, LCP 506 may sense a plurality of atrial events (1302). For example, LCP 506 may be implanted in an atrium of heart 510 and may be configured to sense atrial events. LCP 506 may additionally be configured to communicate, to LCP 502, an indication of one or more of the plurality of sensed atrial events (1304). For example, LCP 502 and LCP 506 may be communicatively coupled. Accordingly, LCP 506 may communicate sensed atrial events to LCP 502 via a communication pathway. One or both of LCP 502 and LCP 506 may additionally be configured to determine an atrial interval between successive sensed atrial events (1306). For example, LCP 502 and/or LCP 506 may be configured to monitor a period of time between successive atrial events. LCP 506 may monitor a period of time between successive sensed atrial events while LCP 502 may monitor a period of time between successive communicated sensed atrial events. In some examples, LCP 502 and/or LCP 506 may be configured to monitor periods of time between two successive atrial events. In other examples, LCP 502 and/or LCP 506 may be configured to monitor periods of time between three, five, ten, or any suitable number of atrial events. LCP 502 and/or LCP 506 may be configured to determine a single atrial interval based on the monitored periods of time, for example by averaging the monitored periods of time. LCP 502 and/or LCP 506 may additionally be configured to determine whether the atrial interval indicates an atrial contraction rate that is above a threshold (1308). For example, LCP 502 and/or LCP 506 may be configured to compare the determined atrial interval to a threshold. In some examples, LCP 502 and/or LCP 506 may determine an atrial contraction rate based on the determined atrial interval. In such examples, LCP 502 and/or LCP 506 may compare the determined atrial contraction rate to the threshold.

If the atrial contraction rate is below the threshold, LCP 502 may be configured to deliver one or more pacing pulses to a ventricle of heart 510 according to a first therapy protocol (1310). In some examples, the first therapy protocol may correspond to a tracking mode. In a tracking mode, LCP 502 may be configured to deliver one or more pacing pulses for each sensed atrial event received from LCP 506. If the atrial contraction rate is above the threshold, LCP 502 may be configured to deliver one or more pacing pulses to the ventricle of heart 510 according to a second therapy protocol (1312). For example, the second therapy protocol may correspond to any of the non-tracking modes described previously with respect to FIGS. 7-11, for instance an ATR mode and/or any other suitable non-tracking mode as desired.

Those skilled in the art will recognize that the present disclosure may be manifested in a variety of forms other than the specific embodiments described and contemplated herein. As one example, as described herein, various examples include one or more modules described as performing various functions. However, other examples may include additional modules that split the described functions up over more modules than that described herein. Additionally, other examples may consolidate the described functions into fewer modules. Accordingly, departure in form and detail may be made without departing from the scope and spirit of the present disclosure as described in the appended claims.

Additional Examples

In a first example, a leadless cardiac pacemaker system comprises a first leadless cardiac pacemaker (LCP) implantable at a ventricular site, a second leadless cardiac pacemaker (LCP) implantable at an atrial site, the second LCP configured to sensing atrial contractions, the first LCP and the second LCP are configured to be communicatively coupled such that the first LCP and the second LCP can deliver pacing therapy to the ventricular site in a tracking mode, and wherein the first LCP and/or the second LCP are configured to deliver pacing therapy to the ventricular site in a non-tracking mode if an interval between atrial contractions sensed by the second LCP becomes shorter than a threshold duration.

In a second example, the leadless cardiac pacemaker system of the first example may further comprise wherein the first LCP is configured to determine if the interval between atrial contractions sensed by the second LCP becomes shorter than a threshold duration and change the leadless cardiac pacemaker system from the tracking mode to the non-tracking mode.

In a third example, the leadless cardiac pacemaker system of any of the first or second examples may further comprise wherein the second LCP is configured to determine if the interval between atrial contractions sensed by the second LCP becomes shorter than a threshold duration and change the leadless cardiac pacemaker system from the tracking mode to the non-tracking mode.

In a fourth example, the leadless cardiac pacemaker system of any of the first through third examples may further comprise wherein the first LCP and/or the second LCP are configured to determine if the interval between atrial contractions sensed by the second LCP becomes shorter than a threshold duration, and are configured to collectively change the leadless cardiac pacemaker system from the tracking mode to the non-tracking mode.

In a fifth example, a method of delivering pacing pulses to a heart of a patient comprises, sensing two or more atrial events by a first implantable medical device, determining, by the first implantable medical device, an atrial interval between successive atrial events, determining, by the first implantable medical device, whether the atrial interval indicates an atrial contraction rate that is above a threshold, if the atrial contraction rate is below the threshold, communicating the sensed atrial events from the first implantable medical device to a second implantable medical device, wherein the second implantable medical device is configured to pace a ventricle of the heart in response to the communicated events in a tracking mode, and if the atrial contraction rate that is above the threshold, communicating from the first implantable medical device to the second implantable medical device a command to pace the ventricle of the heart in a non-tracking mode.

In a sixth example, the method of the fifth example may further comprise wherein if the atrial contraction rate is below the threshold, the second implantable medical device is configured to pace the ventricle of the heart in response to each communicated sensed event in the tracking mode.

In a seventh example, the method of any of the fifth and sixth examples may further comprise wherein if the atrial contraction rate is above the threshold, the second implantable medical device is configured to pace the ventricle of the heart at a predetermined rate in the non-tracking mode.

In an eighth example, the method of any of the fifth through seventh examples may further comprise wherein if the atrial contraction rate is above the threshold but then falls below the threshold, the second implantable medical device is configured to pace the ventricle of the heart in response to each communicated sensed event in the tracking mode.

In a ninth example, a method of delivering pacing pulses to a heart of a patient comprises sensing a plurality of atrial events by a first implantable medical device, communicating, by the first medical device to a second implantable medical device, an indication of one or more of the plurality of sensed atrial events, determining an atrial interval between successive sensed atrial events, determining whether the atrial interval indicates an atrial contraction rate that is above a threshold, if the atrial contraction rate is below the threshold, delivering one or more pacing pulses to a ventricle of the heart of the patient by the second implantable medical device according to a first therapy protocol, and if the atrial contraction rate is above the threshold, delivering one or more pacing pulses to the ventricle of the heart of the patient by the second implantable medical device according to a second therapy protocol.

In a tenth example, the method of the ninth example further comprising wherein the first therapy protocol comprises delivering a pacing pulse to the ventricle of the heart of the patient in response to each sensed atrial event in a tracking mode.

In an eleventh example, the method of any of the ninth or tenth examples further comprises wherein the second therapy protocol comprises delivering one or more pacing pulses to the heart of the patient at a predetermined rate in a non-tracking mode.

In a twelfth example, the method of any of the ninth through eleventh examples further comprising wherein the first implantable medical device determines whether the atrial interval indicates the atrial contraction rate that is above a threshold, if the first implantable medical device determines that the atrial contraction rate that is above the threshold: communicating from the first implantable medical device to the second implantable medical device a first command to begin delivering one or more pacing pulses according to the second therapy protocol, and not communicating the sensed atrial events from the first implantable medical device to the second implantable medical device, and if the first implantable medical device determines that the atrial contraction rate subsequently falls below the threshold: communicating from the first implantable medical device to the second implantable medical device a second command to stop the second implantable medical device from delivering one or more pacing pulses according to the second therapy protocol and returning to the first therapy protocol.

In a thirteenth example, the method of any of the ninth through twelfth examples further comprises wherein determining whether the atrial contraction rate is above a threshold comprises averaging two or more previous atrial intervals.

In a fourteenth example, the method of any of the ninth through thirteenth examples further comprises wherein the first implantable medical device is a leadless cardiac pacemaker (LCP) positioned in or proximate an atrium of the patient's heart.

In a fifteenth example, the method of any of the ninth through fourteenth examples further comprises wherein the second implantable medical device is a leadless cardiac pacemaker (LCP) positioned in or proximate a ventricle of the patient's heart.

In a sixteenth example, the method of any of the ninth through fifteenth examples further comprises wherein communicating, by the first medical device to the second implantable medical device, an indication of one or more of the plurality of sensed atrial events comprises conductive communication through the patient's tissue.

In a seventeenth example, a medical device system for delivering pacing pulses to a heart of a patient, the medical device system comprising a first implantable medical device communicatively coupled to a second implanted medical device, wherein: the first implantable medical device is configured to: sense atrial events; determine, based on the sensed atrial events; an atrial contraction rate; determine whether the atrial contraction rate is above a threshold; if the atrial contraction rate is below the threshold; communicate each sensed atrial event to the second implantable medical device; and if the atrial contraction rate is above the threshold; communicate one sensed atrial event per first predetermined time period to the second implantable medical device, and the second implantable medical device is configured to deliver a pacing pulse in response to receiving a sensed atrial event.

In an eighteenth example, the medical device system of the seventeenth example further comprises wherein communicating one sensed atrial event per first predetermined time period to the second implantable medical device comprises communicating a sensed atrial event after a blanking period following a previous sensed atrial event.

In a nineteenth example, the medical device system of any of the seventeenth and eighteenth examples further comprises wherein communicating one sensed atrial event per first predetermined time period to the second implantable medical device comprises communicating an artificial sensed atrial event to the second implantable medical device once per first predetermined time period.

In a twentieth example, the medical device system of any of the seventeenth through nineteenth examples further comprises wherein the first implantable medical device is further configured to communicate an artificial sensed atrial event to the second implantable medical device if the first implantable medical device does not sense an atrial event within a second predetermined time period following a blanking period.

In a twenty-first example, a leadless cardiac pacemaker system comprises a first leadless cardiac pacemaker (LCP) implantable at a ventricular site, a second leadless cardiac pacemaker (LCP) implantable at an atrial site, the second LCP configured to sensing atrial contractions, the first LCP and the second LCP are configured to be communicatively coupled such that the first LCP and the second LCP can deliver pacing therapy to the ventricular site in a tracking mode, and wherein the first LCP and/or the second LCP are configured to deliver pacing therapy to the ventricular site in a non-tracking mode if an interval between atrial contractions sensed by the second LCP becomes shorter than a threshold duration.

In a twenty-second example, leadless cardiac pacemaker system of the twenty-first example further comprises wherein the first LCP is configured to determine if the interval between atrial contractions sensed by the second LCP becomes shorter than a threshold duration and change the leadless cardiac pacemaker system from the tracking mode to the non-tracking mode.

In a twenty-third example, the leadless cardiac pacemaker system of any of the twenty-first and twenty-second examples further comprises wherein the second LCP is configured to determine if the interval between atrial contractions sensed by the second LCP becomes shorter than a threshold duration and change the leadless cardiac pacemaker system from the tracking mode to the non-tracking mode.

In a twenty-fourth example, the leadless cardiac pacemaker system of any of the twenty-first through twenty-third examples further comprises wherein the first LCP and/or the second LCP are configured to determine if the interval between atrial contractions sensed by the second LCP becomes shorter than a threshold duration, and are configured to collectively change the leadless cardiac pacemaker system from the tracking mode to the non-tracking mode.

In a twenty-fifth example, the leadless cardiac pacemaker system of claim of any of the twenty-first, twenty-third, and twenty-fourth examples further comprising wherein the second LCP communicates a signal to the first LCP to switch from the tracking mode to the non-tracking mode.

In a twenty-sixth example, the leadless cardiac pacemaker system of any of the twenty-first through twenty-fifth examples further comprises wherein in the tracking mode, the second LCP communicates an event signal for each sensed atrial contraction to the first LCP.

In a twenty-seventh example, the leadless cardiac pacemaker system of any of the twenty-first through twenty-sixth examples further comprises wherein in the tracking mode, the first LCP is configured to deliver electrical stimulation in response to each received event signal from the second LCP.

In a twenty-eighth example, the leadless cardiac pacemaker system of any of the twenty-first through twenty-seventh examples further comprises wherein in the non-tracking mode, the first LCP is configured to deliver electrical stimulation independent of any received signals from the second LCP.

In a twenty-ninth example, the leadless cardiac pacemaker system of any of twenty-first through twenty-eighth examples further comprises wherein in the non-tracking mode, the first LCP delivers electrical stimulation at a predefined rate.

In thirtieth example, the leadless cardiac pacemaker system of any of the twenty-first through twenty-ninth examples further comprises wherein in the non-tracking mode, the second LCP does not communicate an event signal for each sensed atrial contraction to the first LCP.

In thirty-first example, the leadless cardiac pacemaker system of any of the twenty-first through thirtieth examples further comprises wherein in the non-tracking mode, the second LCP communicates event signals which represent artificial atrial contractions to the first LCP.

In a thirty-second example, the leadless cardiac pacemaker system of any of the twenty-first through thirty-first examples further comprises wherein the first LCP may deliver electrical stimulation no faster than a predefined rate.

In a thirty-third example, the leadless cardiac pacemaker system of any of the twenty-first through thirty-second examples further comprises wherein determining whether the interval between atrial contractions sensed by the second LCP becomes shorter than a threshold duration comprises averaging two or more previous atrial intervals.

In a thirty-fourth examples, the leadless cardiac pacemaker system of any of the twenty-first through thirty-third examples further comprises wherein the first LCP and the second LCP are configured to be conductively communicatively coupled through a body of a patient.

In a thirty-fifth examples, the leadless cardiac pacemaker system of any of the twenty-first through thirty-fourth examples further comprises wherein after switching from the tracking to the non-tracking mode, the first LCP is configured to slowly reduce a rate of delivered electrical stimulation down to a predefined rate.

What is claimed is:

1. A leadless cardiac pacemaker system comprising:
   a first leadless cardiac pacemaker (LCP) configured to be implantable at a ventricular site;
   a second leadless cardiac pacemaker (LCP) configured to be implantable at an atrial site, the second LCP configured to sense atrial contractions;
   the first LCP and the second LCP are configured to be communicatively coupled such that the second LCP can communicate sensed atrial contractions to the first LCP;
   the first LCP being configured to determine an interval between the atrial contractions that are sensed by the second LCP, the first LCP further configured to change a currently active mode of the leadless cardiac pacemaker system from a tracking mode to a non-tracking mode if the determined interval between the atrial contractions becomes shorter than a lower threshold duration;
   wherein the first LCP delivers pacing therapy to the ventricular site in accordance with the currently active mode of the leadless cardiac pacemaker system; and
   wherein the first LCP delivers pacing therapy to the ventricular site at a predetermined pacing rate if the determined interval between the atrial contractions becomes longer than an upper threshold duration as a result of loss of communication between the first LCP and the second LCP.

2. The leadless cardiac pacemaker system of claim 1, wherein the first LCP is further configured to change the currently active mode of the leadless cardiac pacemaker system from the non-tracking mode to the tracking mode if the determined interval between the atrial contractions becomes longer than the threshold duration.

3. The leadless cardiac pacemaker system of claim 1, wherein in the tracking mode, the first LCP delivers a pacing pulse to the ventricular site in response to each of the atrial contractions communicated by the second LCP.

4. The leadless cardiac pacemaker system of claim 1, wherein in the non-tracking mode, the first LCP delivers pacing pulses to the ventricular site at a predetermined pacing rate.

5. A method of delivering pacing pulses to a heart of a patient, the method comprising:
sensing two or more atrial events by a first implantable medical device implanted at an atrial site;
determining, by the first implantable medical device, an atrial interval between successive atrial events;
determining, by the first implantable medical device, whether the atrial interval indicates an atrial contraction rate that is above a threshold;
if the atrial contraction rate is below the threshold, communicating the sensed atrial events from the first implantable medical device to a second implantable medical device implanted at a ventricular site, wherein the second implantable medical device is configured to pace a ventricle of the heart in response to the communicated events in a tracking mode;
if the atrial contraction rate that is above the threshold, communicating from the first implantable medical device to the second implantable medical device a command to pace the ventricle of the heart in a non-tracking mode; and
in response to a loss of communication between the first implantable medical device and the second implantable medical device, the second implantable medical device is configured to pace the ventricle of the heart at a predetermined safe rate.

6. The method of claim 5, wherein if the atrial contraction rate is below the threshold, the second implantable medical device is configured to pace the ventricle of the heart in response to each communicated sensed event in the tracking mode.

7. The method of claim 5, wherein if the atrial contraction rate is above the threshold, the second implantable medical device is configured to pace the ventricle of the heart at a predetermined rate in the non-tracking mode.

8. The method of claim 7, wherein if the atrial contraction rate is above the threshold but then falls below the threshold, the second implantable medical device is configured to pace the ventricle of the heart in response to each communicated sensed event in the tracking mode.

9. A method of delivering pacing pulses to a heart of a patient, the method comprising:
sensing a plurality of atrial events by a first implantable medical device;
communicating, by the first medical device to a second implantable medical device, an indication of one or more of the plurality of sensed atrial events;
determining an atrial interval between successive sensed atrial events;
determining whether the atrial interval indicates an atrial contraction rate that is above a threshold;
if the atrial contraction rate is below the threshold, delivering one or more pacing pulses to a ventricle of the heart of the patient by the second implantable medical device according to a first therapy protocol;
if the atrial contraction rate is above the threshold, delivering one or more pacing pulses to the ventricle of the heart of the patient by the second implantable medical device according to a second therapy protocol;
wherein the first implantable medical device is configured to determine whether the atrial contraction rate is above the threshold, and if the first implantable medical device determines that the atrial contraction rate is above the threshold:
communicating from the first implantable medical device to the second implantable medical device a first command to begin delivering one or more pacing pulses according to the second therapy protocol, and not communicating the sensed atrial events from the first implantable medical device to the second implantable medical device in order to conserve energy that would otherwise be consumed by communicating through the body from the first implantable medical device to the second implantable medical device; and
if the first implantable medical device determines that the atrial contraction rate subsequently falls below the threshold; and
communicating from the first implantable medical device to the second implantable medical device a second command to stop the second implantable medical device from delivering one or more pacing pulses according to the second therapy protocol and returning to the first therapy protocol.

10. The method of claim 9, wherein the first therapy protocol comprises delivering a pacing pulse to the ventricle of the heart of the patient in response to each sensed atrial event in a tracking mode.

11. The method of claim 9, wherein the second therapy protocol comprises delivering one or more pacing pulses to the heart of the patient at a predetermined rate in a non-tracking mode.

12. The method of claim 9, wherein determining whether the atrial contraction rate is above a threshold comprises averaging two or more previous atrial intervals.

13. The method of claim 9, wherein the first implantable medical device is a leadless cardiac pacemaker (LCP) positioned in or proximate an atrium of the patient's heart.

14. The method of claim 9, wherein the second implantable medical device is a leadless cardiac pacemaker (LCP) positioned in or proximate a ventricle of the patient's heart.

15. The method of claim 9, wherein communicating, by the first medical device to the second implantable medical device, an indication of one or more of the plurality of sensed atrial events comprises conductive communication through the patient's tissue.

16. A medical device system for delivering pacing pulses to a heart of a patient, the medical device system comprising:
a first implantable medical device implantable at an atrial site and communicatively coupled to a second implanted medical device implantable at a ventricular site, wherein:
the first implantable medical device is configured to:
sense atrial events;
determine, based on the sensed atrial events, an atrial contraction rate;
determine whether the atrial contraction rate is above a threshold;
if the atrial contraction rate is below the threshold, communicate each sensed atrial event to the second implantable medical device; and
if the atrial contraction rate is above the threshold, communicate an artificial sensed atrial event per a first predetermined time period to the second implantable medical device, and
the second implantable medical device is configured to operate in a tracking mode and deliver a pacing pulse in response to receiving each sensed atrial event and in response to receiving each artificial sensed atrial event.

17. The medical device system of claim 16, wherein communicating the artificial sensed atrial event per the first predetermined time period to the second implantable medical device comprises communicating a sensed atrial event after a blanking period following a previous sensed atrial event.

18. The medical device system of claim 16, wherein communicating the artificial sensed atrial event per the first predetermined time period to the second implantable medical device comprises communicating an artificial sensed atrial event to the second implantable medical device once per first predetermined time period.

19. The medical device system of claim 18, wherein the first implantable medical device is further configured to communicate an artificial sensed atrial event to the second implantable medical device if the first implantable medical device does not sense an atrial event within a second predetermined time period following a blanking period as a result of a loss of communication between the first implantable medical device and the second implantable medical device.

\* \* \* \* \*